United States Patent
Velghe et al.

(10) Patent No.: US 7,235,215 B2
(45) Date of Patent: Jun. 26, 2007

(54) CAPILLARY FILLER

(75) Inventors: Franck Velghe, Astene-Deinze (BE); Werner René Irène De Beukeleer, Vremde (BE); Ignace Maria S. M. Van De Maele, Waregem (BE)

(73) Assignee: Tibotec BVBA, Mechelen (BE)

( * ) Notice: Subject to any disclaimer, the term of this patent is extended or adjusted under 35 U.S.C. 154(b) by 520 days.

(21) Appl. No.: 10/363,229

(22) PCT Filed: Sep. 7, 2001

(86) PCT No.: PCT/EP01/10394

§ 371 (c)(1),
(2), (4) Date: Mar. 5, 2003

(87) PCT Pub. No.: WO02/21143

PCT Pub. Date: Mar. 14, 2002

(65) Prior Publication Data

US 2003/0180189 A1    Sep. 25, 2003

(30) Foreign Application Priority Data

Sep. 7, 2000   (EP)   ................................ 002030831

(51) Int. Cl.
*B01L 3/02* (2006.01)
*G01N 1/10* (2006.01)
*B65B 1/04* (2006.01)
*B65B 3/04* (2006.01)
*B65B 37/00* (2006.01)

(52) U.S. Cl. .................. 422/100; 422/62; 422/63; 422/64; 422/65; 422/66; 422/67; 436/180; 141/238

(58) Field of Classification Search .......... 422/99–100, 422/63–67; 141/238; 436/180
See application file for complete search history.

(56) References Cited

U.S. PATENT DOCUMENTS

| | | | |
|---|---|---|---|
| 3,788,370 A * | 1/1974 | Hare et al. ................... | 141/125 |
| 3,915,652 A | 10/1975 | Natelson | |
| 4,256,153 A * | 3/1981 | Lamaziere ................... | 141/84 |
| 4,960,566 A | 10/1990 | Mochida | |
| 5,139,056 A * | 8/1992 | Sagawa et al. ................ | 141/1 |
| 5,226,462 A * | 7/1993 | Carl .............................. | 141/1 |
| 5,356,525 A | 10/1994 | Goodale et al. | |
| 5,798,035 A | 8/1998 | Kirk et al. | |
| 6,083,763 A | 7/2000 | Balch | |
| 6,368,872 B1 * | 4/2002 | Juranas ........................ | 436/180 |
| 6,599,476 B1 * | 7/2003 | Watson et al. ................ | 422/63 |
| 2003/0138355 A1 * | 7/2003 | Tamura et al. ................ | 422/63 |
| 2004/0081590 A1 * | 4/2004 | Ward, Jr. ...................... | 422/104 |

FOREIGN PATENT DOCUMENTS

| | | |
|---|---|---|
| EP | 0745855 A2 | 12/1996 |
| EP | 0409606 B1 | 9/1997 |
| WO | WO 00/14540 A1 | 3/2000 |

* cited by examiner

*Primary Examiner*—Brian R. Gordon
(74) *Attorney, Agent, or Firm*—Yunling Ren

(57) ABSTRACT

A capillary filling system automatically plucks capillaries from a capillary roll, and transports them to a filling station where the capillaries are filled with compounds. The filled capillaries are then fixed on a template where they are then ready to be used for experimentation. A method of filling the capillaries is also disclosed.

14 Claims, 15 Drawing Sheets

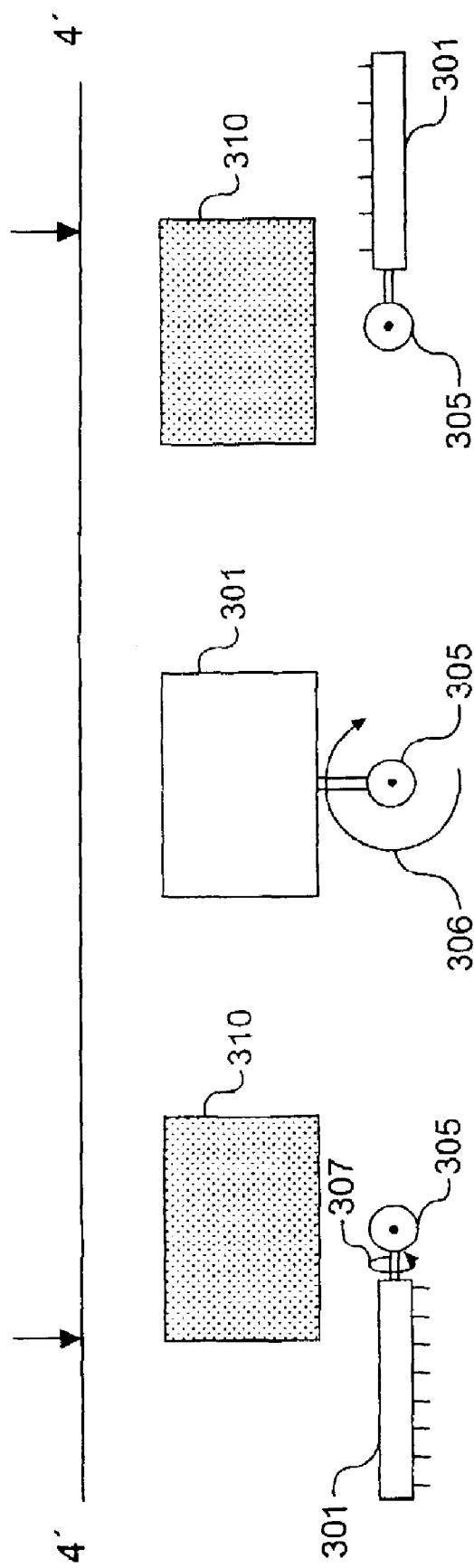

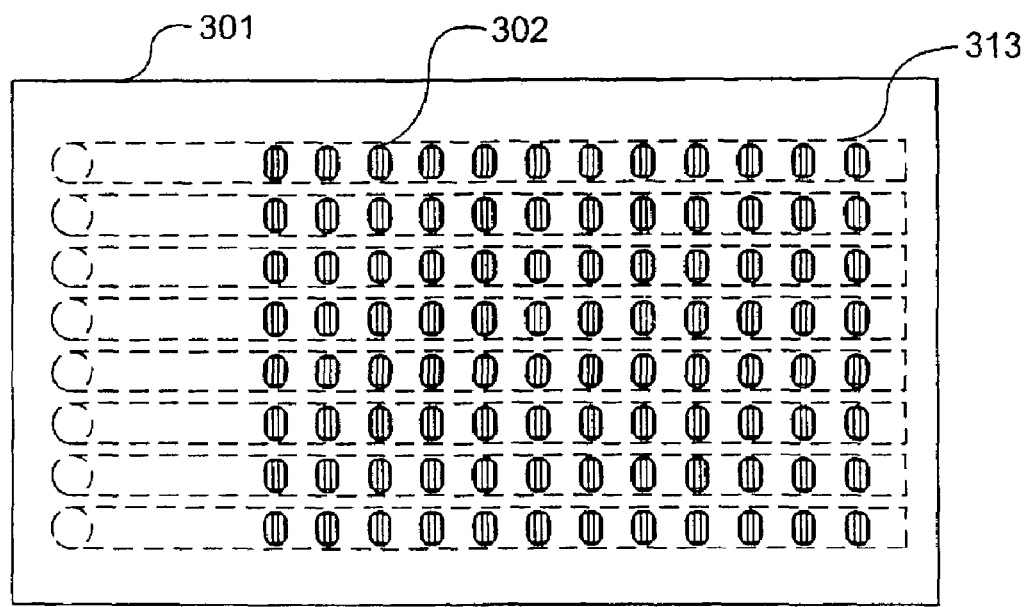
FIG. 11
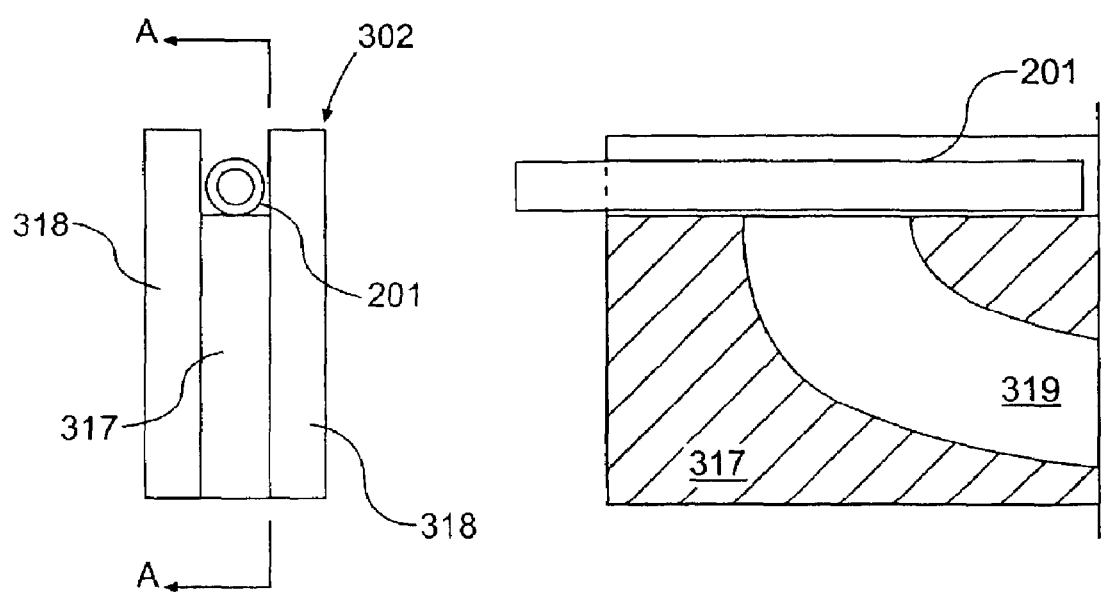
FIG. 12A   FIG. 12B

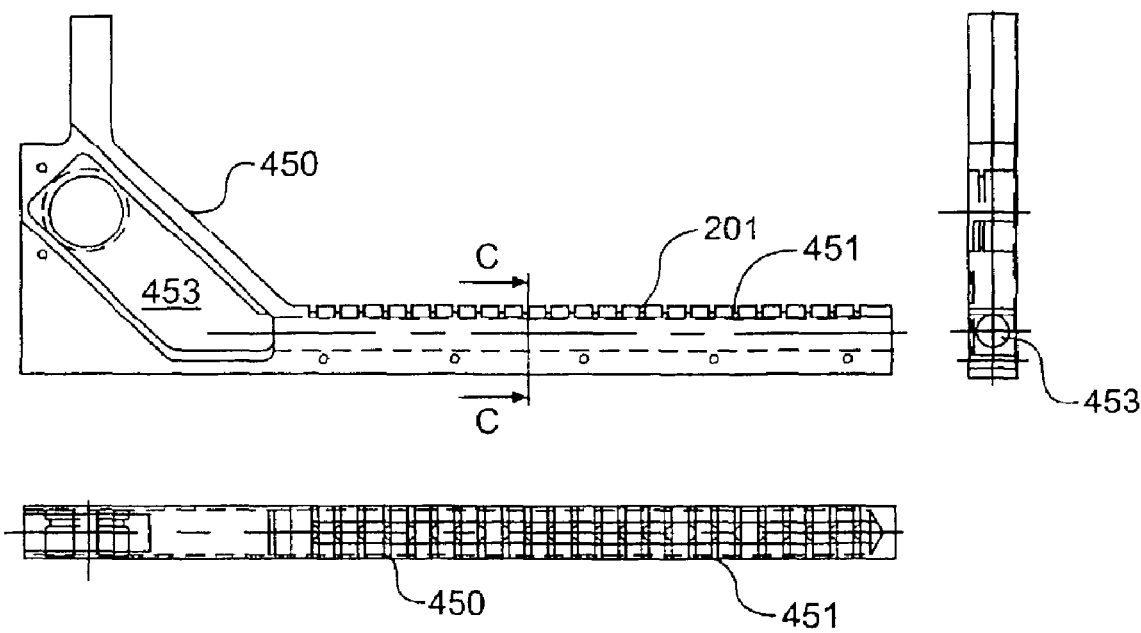
FIG. 14A
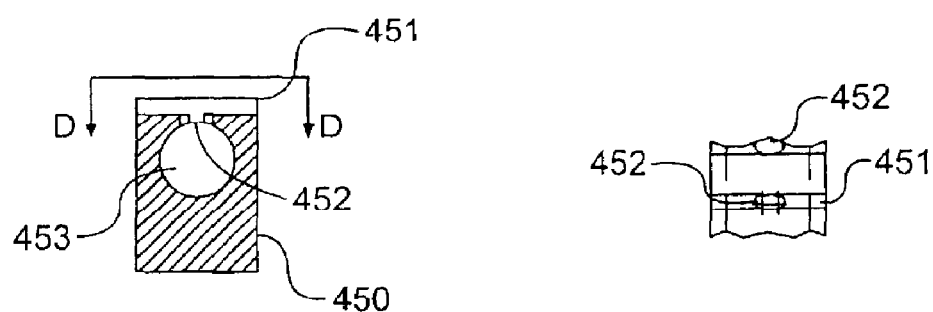
VIEW C-C
FIG. 14B
VIEW D-D
FIG. 14C

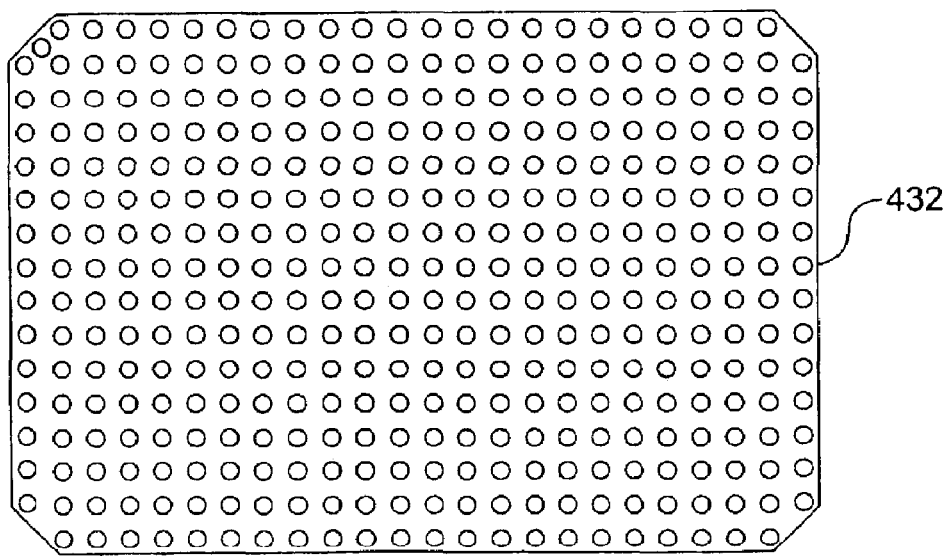
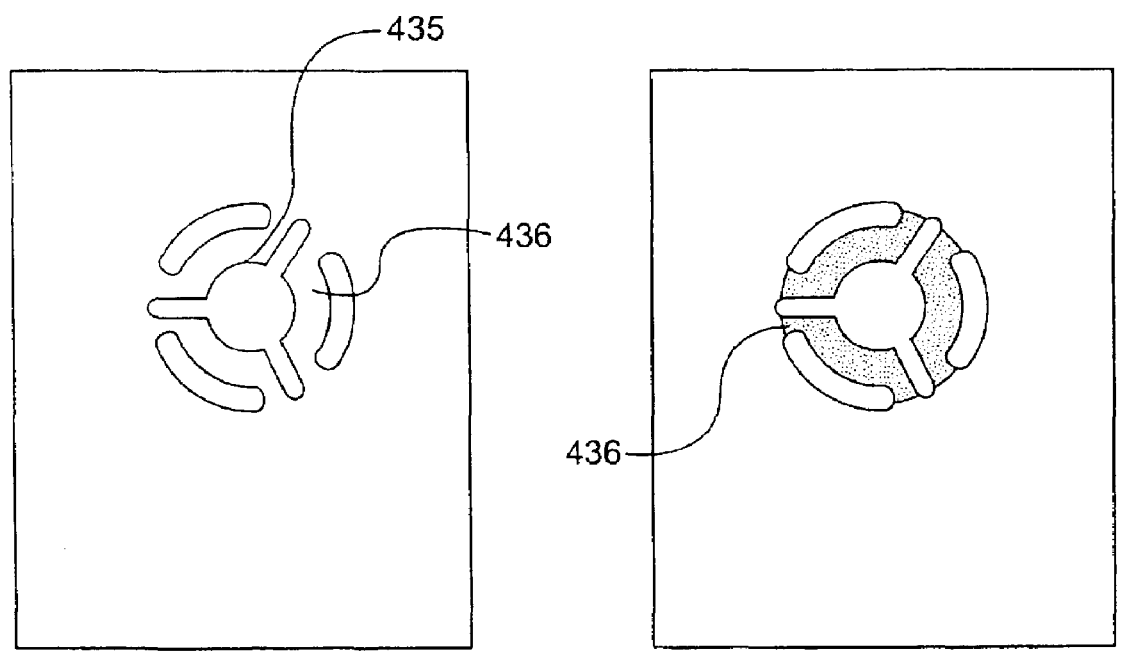
FIG. 15

CAPILLARY FILLER

CROSS REFERENCE TO RELATED APPLICATIONS

This Application is a National Stage Application under 35 U.S.C. § 371 of PCT/EP01/10394, filed Sep. 7, 2001, which claims priority to European Patent Application EP 00203083.1, filed on Sep. 7, 2000, all of which are incorporated herein by reference in their entirety.

BACKGROUND OF THE INVENTION

1. Field of the Invention

The present invention relates to systems and methods for filling capillaries, and more specifically to such systems and methods for preparing a matrix of filled capillaries for use in screening systems and methods. In particular, the present invention further relates to systems and methods that facilitate the preparation of a matrix of capillaries filled from a standard library plate.

2. Description of Related Art

Currently, screening programs identify potential compounds for use as drugs. Specifically, drug discovery often depends on high throughput screening (HTS) techniques to screen compounds, such as liquid analytes, as potential drug candidates. In HTS, an increasingly high number of compounds, most often organized in libraries, are tested simultaneously. A library of compounds may be stored in a standard multiwell plate, hereinafter referred to as a standard library plate.

Simultaneous testing of a high number of compounds is due, at least in part, to technological developments, such as automated testing, combinatorial chemistry, and the polymerase chain reaction. An increased demand for new and better drugs for a variety of diseases also drives the need for HTS techniques, including simultaneous testing of a high number of compounds.

A current standard multiwell plate or microtiter plate, such as the multiwell plate commonly used in the screening industry for use in HTS, has dimensions of 127.8 mm by 85.5 mm. For the standard multiwell plate, the number of wells per plate, i.e., the density, has evolved over the years from a density of 16 wells per plate to 96 wells per plate, and in some instances, to 384 wells per plate. The most commonly use standard multiwell plate today has a density of 96 wells per plate. The centerline-to-centerline distance between wells in this standard 96 well plate is typically on the order of 9 mm. HTS systems have been developed for use with the format of the standard multiwell plate. However, for increasing throughput requirements and simultaneous testing of more compounds, there is a trend in HTS to use higher density plates with, for example, 384, 864, 1536, and 9600 wells.

The use of these increased density plates present new problems. Particularly, the transfer of compounds into the plate limits the testing process, as the compounds have to be brought in at a high density using various different geometries. Subsequent dispensing of solutions onto these high density plates during the testing process also poses difficulties. In addition, the introduction of robots and other forms of automation in drug discovery has led to new concerns, such as, for example, concerns regarding the speed, parallelization, volume, and reliability of robotic systems.

Current transfer and dispensing systems often rely on glass pipettors with plungers (such as the Hydrasystem™ of Robin Scientific Inc.), needles or pins, or piezo-electric pipettors. Each such system has drawbacks. For example, current pipetting systems include the relatively high cost of pipet tips, which can be substantial in automated testing. The use of needles and pins for liquid dispensing, although less expensive, lacks control over the dispensed volume and does not provide for multiple replicas to be made. Current piezo-electric pipettors usually provide increased control over dispensed volume, but typically are relatively large, difficult to miniaturize, and not suitable for massive parallel dispensing due to their relative expense. Current glass pipettors, although not as expensive, share many of the disadvantages of current piezo-electric pipettors and may not dispense liquid in volumes as small as 100 nanoliters.

Accordingly, the present invention is directed to a system and process for filling capillaries and preparing a matrix of filled capillaries that substantially obviate one or more of the problems due to limitations and disadvantages of the related art. In accordance with the principles of the invention, a system is provided for preparing a matrix of filled capillaries comprising a loader configured to load a plurality of unfilled capillaries onto a first transporter. In one embodiment of the disclosed system, a manipulator is included and configured to collect the plurality of unfilled capillaries from the first transporter, fill the capillaries with a solution, and load the filled capillaries onto a second transporter. A matrix packer subsytem is also included and configured to collect the filled capillaries from the second transporter and feed the filled capillaries onto a matrix template.

BRIEF SUMMARY OF THE INVENTION

According to an embodiment of the invention, a fixer may be configured to affix the filled capillaries onto the template.

According to a further embodiment of the invention, the first and second transporters are conveyors. In an even further embodiment, the unfilled capillaries are contained in a rolling tape in the loader. In still another embodiment of the invention, the loader includes an unwinder to unwind the rolling tape, a mechanism to release the capillaries from the rolling tape, and a winder for rewinding the rolling tape after the capillaries are released.

In another embodiment of the invention, the manipulator has multiple degrees of freedom. According to another embodiment, the manipulator is capable of turning on a vertical axis between the operations of collecting, filling, and loading the capillaries.

In another embodiment, the manipulator collects the capillaries from the first transporter with fingers. In a further embodiment of the invention, the fingers are actuated by a vacuum mechanism. In an even further embodiment of the invention, the manipulator has an array of fingers capable of holding a plurality of capillaries via a vacuum or low pressure generated airflow.

According to still another embodiment of the invention, the first transporter contains a plurality of equidistant spaces. The distance between the spaces on the first transporter may be substantially equal to a distance between the unfilled capillaries on a rolling tape. Further, the manipulator may contain a plurality of equidistant vacuum fingers configured to receive capillaries, and the distance between the spaces on the first transporter may be substantially equal to a distance between the vacuum fingers. In yet another embodiment of the invention, the second transporter contains a plurality of equidistant spaces, and the distance between the spaces on the first transporter may be substantially equal to the distance between the spaces on the second transporter.

According to a further embodiment of the invention, a drive mechanism to drive the first transporter may be included. In a further embodiment, the first transporter may contain a plurality of equidistant spaces, and the drive mechanism drives the first transporter such that each space receives a single unfilled capillary.

In accordance with the principles of the invention, a method also is provided for making a matrix of filled capillaries. In the disclosed method, a sequence of capillaries on a substrate is provided. The capillaries are removed in sequence from the substrate and are collected on a manipulator. A plurality of capillaries are substantially simultaneously filled with a solution and the filled capillaries are loaded onto a matrix.

In another embodiment of the invention, the capillaries may be filled with a predetermined volume of solution. The filling step may include dipping the capillaries into a plurality of solutions containing compounds. Further, the filled capillaries may be affixed to the matrix.

In yet another embodiment of the invention, the substrate is a roll of tape, and the removing step may comprise unwinding the tape, releasing the capillaries from the tape, and rewinding the tape.

In another embodiment of the invention, the manipulator may be turned on a vertical axis between the operations of collecting, filling, and loading the capillaries.

According to an embodiment of the invention, the manipulator may collect the capillaries with fingers. In another embodiment, the fingers may be actuated by a vacuum mechanism.

In one embodiment of the invention, a method for assembling a holder of filled capillaries is provided. The method may include providing a plurality of unfilled capillaries, collecting at least a portion of the plurality of capillaries, gripping the collected capillaries with a manipulator, filling the gripped capillaries substantially simultaneously with at least one solution, removing the filled capillaries from the manipulator, and inserting the filled capillaries into a holder.

In another embodiment the method may further include loading the plurality of unfilled capillaries one at a time onto a first transporter, and simultaneously collecting at least a portion of the capillaries from the first transporter. The method may even further include unloading the filled capillaries from the manipulator onto a second transporter, and inserting the filled capillaries into a holder. The at least one solution may be provided in a standard multiwell library plate having a first density of wells per plate. The holder may be configured to retain the filled capillaries in an arrangement corresponding to a standard multiwell plate having a second density of wells per plate.

According to one embodiment, the method may include providing a sequence of capillaries on a substrate, and removing the capillaries in sequence from the substrate. The substrate may be a roll of tape, and the removing step may comprise unwinding the tape, releasing the capillaries from the tape, and rewinding the tape. The method may further include retaining the filled capillaries to the holder.

According to another embodiment, the method may even further include moving the manipulator to a first station to collect at least a portion of the plurality of capillaries, moving the manipulator to a second station to fill the collected capillaries, and moving the manipulator to a third station to unload the filled capillaries.

In another embodiment of the invention, a method for creating an array of solution-filled capillaries from unfilled capillaries and a standard multiwell library plate containing one or more solutions in an array of wells is provided. The method may include providing a plurality of capillaries and organizing at least some of said plurality of capillaries into a first array of capillaries. The first array of capillaries configured to dimensionally correspond to the array of wells of the standard multiwell library plate. The method may also include dipping the first array of capillaries into the corresponding array of wells of the standard multiwell library plate containing one or more solutions, filling the first array of capillaries with the solutions from the standard multiwell library plate, and re-organizing the first array of now-filled capillaries at least partially into a second array of capillaries.

In one embodiment, the dimensions of the second array of capillaries may differ from the dimensions of the first array of capillaries. In another embodiment, the first array of capillaries may be arranged in an eight-by-twelve array of ninety-six capillaries. The second array of capillaries may be arranged in a forty-eight-by-thirty-two array of fifteen-hundred thirty-six capillaries. Further, the centerline-to-centerline distance between the capillaries in the first array may be approximately 9 mm, and the centerline-to-centerline distance between the capillaries in the second array may be approximately 2.25 mm.

In another embodiment, the the position of each filled capillary and the identity of the solution within the capillary may be tracked from when the first array of capillaries is filled to when the second array of filled capillaries is created.

According to even another embodiment of the invention, a capillary holder for holding a plurality of filled capillaries is provided. The capillary holder may include a template having a plurality of holes and at least one spring element associated with each hole. The spring elements may be integral with the template. The holes and the spring elements may be formed by photo-etching. Moreover, the spring elements may be elastically deformable.

Additional features and aspects of the invention are set forth in the description which follows, and in part, may be apparent from the description or may be learned by practice of the invention. The features and aspects of the invention may be realized and attained by the systems and methods particularly pointed out in the written description and claims hereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate preferred embodiments of the invention and, together with the description, serve to explain the features and principles of the invention.

In the drawings,

FIG. 3 is a top view of a gripping unit of the capillary filler system of FIG. 1 as it moves through its various stages.

FIG. 11 shows a front view of a plate with fingers of a gripping unit of FIG. 5.

FIGS. 12(a) and 12(b) show a detail of a finger of FIG. 1.

FIG. 14 shows top, front and side views and details of a lifter of FIG. 5.

FIG. 15 shows a front view and details of an exemplary capillary holder.

DETAILED DESCRIPTION OF THE INVENTION

Figure 1:
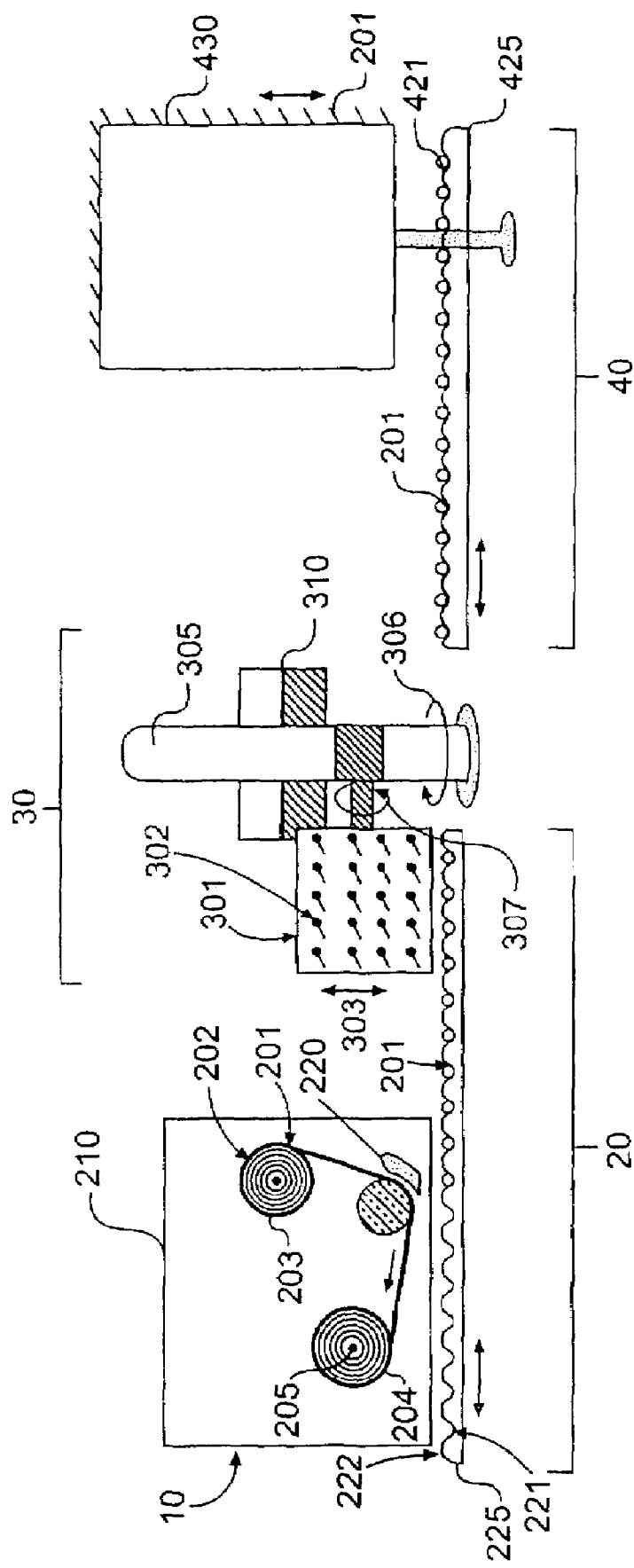
FIG. 1 is a site view of an exemplary capillary filler system according to an embodiment of the present invention.

Reference will now be made in detail to the present preferred embodiments of the invention, examples of which are illustrated in the accompanying drawings.

The present invention relates to systems and methods for creating a matrix of filled capillaries. In one embodiment, an automated system and method may be provided so that unfilled capillaries may be automatically fed onto a first transport system. The transport system may carry the unfilled capillaries to a manipulator that may collect row after row of the unfilled capillaries until the manipulator is fully loaded. The manipulator may use vacuum forces to hold the unfilled capillaries securely in place. The manipulator then may shift in position and dip the unfilled capillaries in a solution or solutions until the capillaries are filled by capillary forces. The manipulator again may shift in position to unload the now-filled capillaries, row by row, onto a second transport system. The second transport system may carry the filled capillaries to a matrix block that receives rows of the filled capillaries. The matrix block collects the capillaries until it is fully loaded, at which time the matrix block of filled capillaries is ready to be used by a subsequent user.

In one embodiment of the present invention, when filling the capillaries with a solution or solutions, the capillaries may be arranged so as to be dipped into the wells of a standard multiwell plate. The current standard multiwell plate is typically approximately 127.8 mm by 85.5 mm. When collected into a matrix block of filled capillaries, the capillaries may also be arranged so as to be used with a standard well test plate, i.e., a plate having the same dimensions as the standard multiwell plate. Furthermore, the standard multiwell plate at the dipping station may have the same or a different well density than the standard well test plate for which the matrix block of filled capillaries is configured. For instance, the standard multiwell plate at the dipping station may have a density of ninety-six wells per plate and the matrix block of filled capillaries may be configured for a standard well test plate having a density of ninety-six wells per plate, 384 wells per plate, 1536 wells per plate, 9600 wells per plate, or any other density. Further, the when collected into a matrix block of filled capillaries, the capillaries may be arranged for used with a non-standard well test plate. Such a non-standard well test plate would have dimensions other than those of the standard multiwell plate. In addition, such a non-standard well test plate could have the same or different density of wells per plate as the standard multiwell plate at the dipping station. Even further, the matrix block of filled capillaries could be arranged for use with a non-standard well test plate having a non-rectangular array of wells. For instance, the filled capillaries in the matrix block could be arranged in a circular pattern for testing with a non-standard well test plate having a corresponding circular pattern of wells.

An exemplary embodiment of a capillary filling system of the present invention is shown in FIG. 1 and is designated generally by reference numeral 10. As embodied herein and referring to FIG. 1, capillary filling system 10 includes several component subsystems which operate in unison to automatically fill one or more capillaries, and preferably prepare a matrix block of filled capillaries. Capillary filling system 10 includes a capillary loader subsystem 20, a capillary filler subsystem 30, and a matrix packing subsystem 40. Each subsystem will be described in detail below.

Capillary loader subsystem 20 detaches individual capillaries 201 from a sequence of capillaries on a substrate, for example as on a tape roll 202, and prepares them for filling. Capillaries 201 may be small glass tubes having an inner diameter smaller than about 1 mm, or, more preferably, smaller than about 0.5 mm, and having a length up to about 10 cm. Other dimensions for the capillary tubes may be suitable as long as the tubes may be filled through capillary action.

Capillaries 201 may be supplied on tape roll 202. Tape roll 202 may contain an adhesive which reversibly binds individual capillaries 201 to a substrate 208. As a protective measure, substrate 208 holding these capillaries may be rolled with the capillaries towards the inside of the roll. Substrate 208 is generally not as wide as the capillaries adhered to the substrate.

Tape roll 202 is loaded onto a loading peg 203 in a loader housing 210. One end of tape roll 202 with capillaries 201 thereon is directed through a collector 220, which removes the capillaries one by one. Tape roll 202 is rewound as a spent tape roll 204 around rewinding peg 205. A motor 209, such as an electric motor, or other similar suitable drive mechanism, turns pegs 203, 205 on which rolls 202, 204 are loaded and serves to keep tape substrate 208 under tension. Another motor 207 pulls the tape from tape roll 202. Collector 220 removes adhered capillaries 201 from substrate 208 as the tape traverses through the collector. By way of example, capillaries 201 may be removed by one or more contact fingers or by using a vacuum force. Vacuum refers to an air pressure less than ambient and vacuum force refers to the forces arising from the flow of air from a region of ambient pressure to a region of the less than ambient pressure.

The loading and rewinding pegs 203, 205 in conjunction with motor 209 ensure that the tape from rolls 202, 204 is kept taut by, for example, driving pegs 203, 205 via a rotary dashpot or a slip coupling, or other similar suitable mechanisms. Keeping the tape from rolls 202, 204 at a constant tension provides for controlled unrolling of roll 202 and rolling of roll 204.

The automation of loader subsystem 20 minimizes operator handling of capillaries 201. The operator need only load tape roll 202 and remove spent roll 204. The automation of the capillary removing mechanism of loader 20 decreases manual operation and associated error. Also, lack of capillary handling by an operator minimizes any possible contamination of capillaries 201 due to manual contact.

Collector 220 removes capillaries 201 from substrate 208 of tape roll 202 and deposits the individual capillaries in open spaces 221 on a sliding toothed conveyor or rack 225. Rack 225 has an individual space 221 between each adjacent tooth 222, each space 221 accommodating a single capillary 201. If a standard ninety-six well-per-plate library plate is to be used to fill the capillaries, then rack 225 may have ninety-six individual spaces. The distance between adjacent spaces 221, and thus, the distance between adjacent capillaries 201 on rack 225, is typically kept at a constant, for example, approximately 2.25 mm for a 1536 template.

Rack 225 is mounted on a first transporter 227. A motor (not shown) or other suitable similar drive mechanism drives transporter 227 beneath collector 220 and each space 221 receives a single capillary 201. The motor speed may be adjusted so as to increase or decrease the rate of capillary loading onto rack 225. Furthermore, the drive mechanism that drives tape 202 and the drive mechanism that drives transporter 227 may be synchronized to remove the capillaries 201 from the tape substrate 208 at the same rate as each space 221 on rack 225 receives a single capillary 201. Alternatively, a single drive mechanism, such as for example a single motor, may be used to both unwind tape 202 and drive transporter 227, or, alternatively, may be used to drive the entire system 10 including all its subsystems 20, 30, 40.

The capillary loader subsystem 20, like the other remaining subsystems to be described, may be fully automated, and is preferably computer controlled. This increases speed of loading and filling capillaries into a matrix block of desired size and minimizes human operation and error.

In accordance with an embodiment of the invention, a first servo-motor, for instance, a direct drive servo-motor, is provided that positions a first space 221 of rack 225 below a collector 220. A second servo-motor unrolls tape roll 202 resulting in the removal of capillaries 201 one at a time from the substrate of tape roll 202 by means of a mechanism, such as plucking mechanism 228 in FIG. 6. The first drive motor then moves transporter 227 into the next position so that a second space 221 on rack 225 is detected below the collector 220. The process of loading repeats until all desired spaces 221 are filled by empty capillaries 201.

Plucking mechanism 228 may be any suitable means for removing capillaries 201 from substrate 208. For instance, a vacuum force may be used to pull each capillary from the substrate; the substrate with attached capillaries may be pulled past a wedge-shaped scraper that gently scrapes the capillary from the substrate; or the substrate with attached capillaries may be pulled through a slot wherein the ends of the capillaries travel through channels that serve to retain the capillaries when the substrate is pulled up and away from the capillaries in a peeling action.

Figure 6:
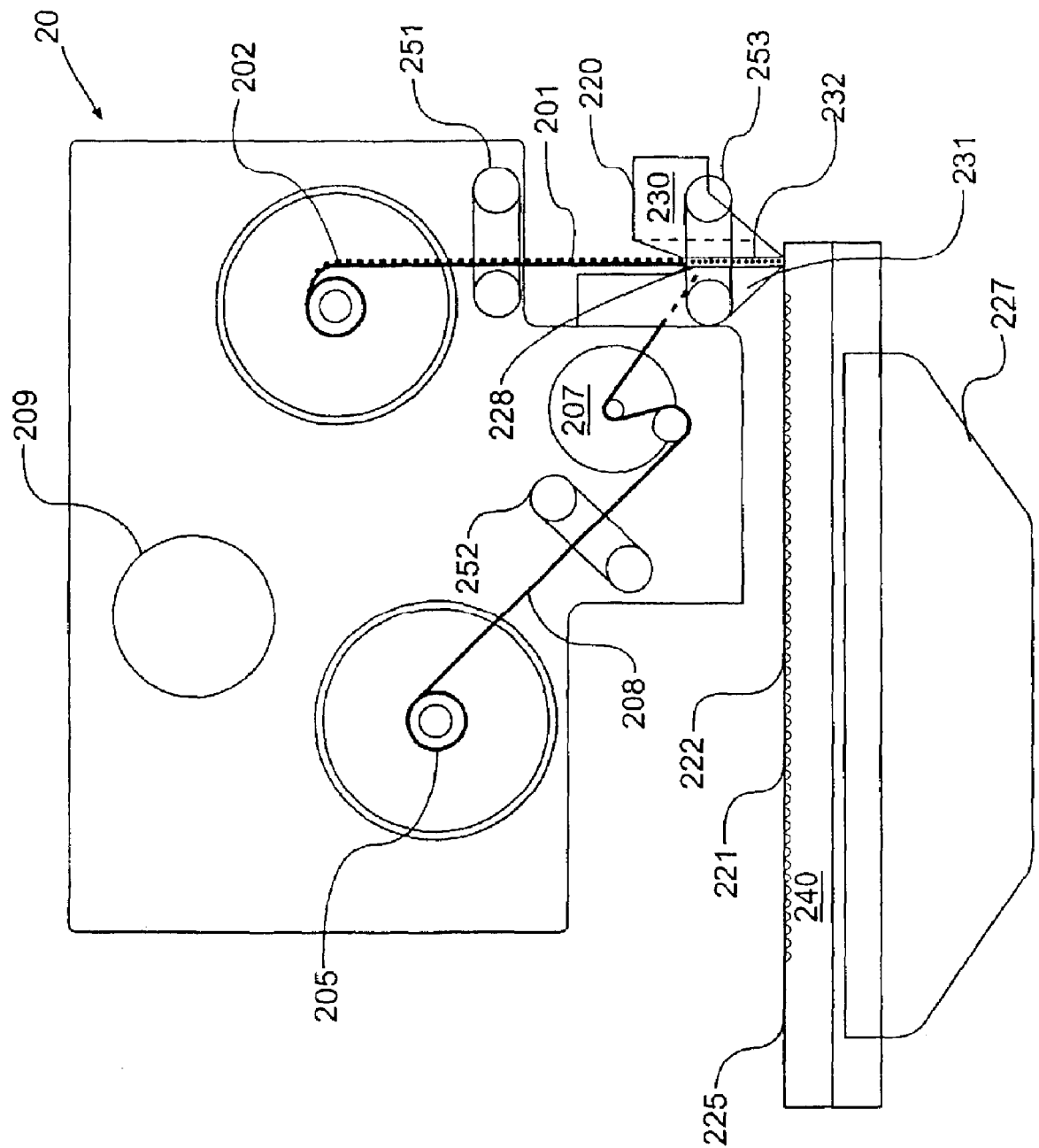
FIG. 6 shows the capillary loader subsystem of FIG. 5.

In accordance with one embodiment, as shown in FIG. 6, collector 220 includes a mobile guide 230 and a fixed guide 231. These guides, in conjunction with the geometry of rack 225, ensure that capillaries 201 are precisely deposited into spaces 221 of rack 225. The tape with attached capillaries 201 coming from tape roll 202 is guided into a narrow slot 232 between guides 230, 231. The width of slot 232 may be altered, for instance by moving mobile guide 230 in towards fixed guide 231. Slot 232 extends from where the tape from roll 202 enters collector 220, past plucking mechanism 228, to where collector 220 contacts, or almost contacts, rack 225. Slot 232 includes two channels configured to retain and guide the ends of capillaries 201 both before and after they are removed from substrate 208. When the capillaries attached to the tape reach plucking mechanism 228, the capillaries are removed from the tape substrate. In this particular embodiment, substrate 208 is peeled up and away from the capillaries in the slot, and the capillaries remain in the slot. The now-individual capillaries drop through the slot, for instance, due to gravity, into a queue of capillaries, for instance two or more capillaries, waiting to be loaded onto rack 225. The queue portion of slot 232 may be wide enough for the capillaries to pass through smoothly, but not so wide as to allow two or more capillaries to jam and block the downward movement of the capillaries. Below collector 220, at the bottom of slot 232 is rack 225.

In accordance with another embodiment, rack 225 is precisely position below slot 232 of collector 220 such that a capillary 201 may not leave slot 232 unless a space 221 is located beneath the slot. In other words, the gap between the bottom of collector 220 and top of teeth 222 is less than the diameter of capillary 201. Thus, as rack 225 moves laterally beneath collector 220, a series of teeth 222 and spaces 221 pass beneath the capillaries queued within slot 232. The capillaries remain in slot 232 when teeth 222 pass beneath slot 232, but fall into spaces 221 when the spaces pass beneath the slot. In order to accommodate only one capillary, spaces 221 may be provided with completely symmetrical profiles which are photo-etched to achieve the desired tolerance. In this manner, each space 221 may be formed so that a capillary within the space fills the space completely. As rack 225 moves laterally beneath collector 220, a capillary 201 within space 221, i.e., a filled space, will prohibit any capillary queued within slot 232 from falling into the filled space. The tolerances are preferably set to minimize the possibility of rack 225 jamming against collector 220 due to any capillary queued within slot 232 partially falling into an already filled space. Moreover, the portion of collector 220 adjacent to and defining the lower edge of slot 232 may be shaped to help guide capillaries 201 into spaces 221 and also help to prevent jams.

Rack 225 may be made out of two plates 240 that are fixed on both sides of the transport table 229. Plates 240 may be formed from stainless steel, brass, plastic or other suitable material. Teeth 222 and open spaces 221 may be formed in these plates. Plates 240, if formed from brass, may have, for instance, a thickness of approximately 0.1 mm and may be as long as the transporter table. The length of plates 240 may be set so as to accommodate a first end region having no spaces defining teeth, a central region having teeth 222 and spaces 221 (for instance, ninety-six spaces), and a second end region also having no spaces defining teeth. When rack 225 is at its leftmost position, the first end region of plates 240 is located under slot 232 of collector 220. Because the first end region has no spaces, no capillaries will fall from the bottom of the capillaries queued in slot 232. As rack 225 moves under collector 220, from the first end region to the second end region, the central region having teeth 222 and spaces 221 passes under slot 232, and capillaries 201 fall into spaces 221. The second end region extends from the last space defined in plates 240 to slightly beyond the point that is under collector 220 when transport table 229 is in its rightmost position. The portion of plates 240 extending slightly beyond the point under collector 220 is a small safety zone used to ensure that errors in the positioning of transport table 229 do not result in capillaries 201 falling out of collector 220 and onto the floor. The rightmost position of transport table 229 occurs when the rightmost space 221 in rack 225 is even with the rightmost finger of manipulator 305, when manipulator 305 is in the first loading position.

In accordance with one embodiment, capillaries 201 may be placed in rack 225 such that approximately 40% of the length of the capillary is located to one side of plates 240. For instance, first plate 240 may support each capillary at a position at approximately 10% of the length of the capillary, and second plate 240 may support the capillary at a position at approximately 55% of its length, thus having approximately 45% of the length of the capillary extend to one side of plates 240. As will be discussed later, this extended portion of the capillary will be held by manipulator 305 of the capillary filler system 30.

In an exemplary operation, the tape with attached capillaries 201 from tape roll 202 is pulled through collector 220 by a motor 207, for instance, a servo-motor. A Programmable Logic Controller (PLC) may control motor 207 as well as other components in system 10. Substrate 208, i.e., the tape without attached capillaries, is recovered by a rewinder or spent tape roll 204. A dashpot motor 209 drives spent tape roll 204. Substrate 208 is maintained under tension.

One detector, for instance, a first laser sensor 251, may be used to detect if the tape with attached capillaries extending between peg 203 and collector 220 has attached capillaries, or alternatively, if the tape still extends between peg 203 and collector 220. Another detector, for instance, a second laser sensor 252, may be used to detect if substrate 208 extends between collector 220 and peg 205. If either of these detectors fail to detect their corresponding tape, an error signal is transmitted to a controller, such as the PLC unit, and servo-motor 207 is not run.

Another detector, such as a third laser sensor 253, may check if the capillary queue in collector 220 is filled. If this third sensor does not detect any capillaries in the queue, it may send a signal to the PLC unit to cause motor 207 to start pulling the tape with attached capillaries into collector 220, where the capillaries 201 will be removed from the tape and added to the queue. Alternatively, third sensor 253 could be set at a height to detect a particular capillary in the queue, for instance the tenth capillary from the bottom, and to send a signal when that particular capillary is not detected. When third sensor 253 detects a capillary 201, a signal may be sent to servo-motor 207 to stop. Third sensor 253 safeguards against too many capillaries piling up and jamming collector 220.

An electric motor may drive a spindle (not shown) on which the transport table 229 is fixed. The accuracy with which the transport table 229 and rack 225 may be positioned, during the loading process, will typically be on the order of 0.1 mm. A motor coupled to first transporter 227 now positions a first leftmost space 221 of rack 225 beneath slot 232 of collector 220 to cause a single capillary 201 to fall into this first space. Transporter 227 with rack 225 is laterally moved to the left so that a second space, consecutive to the first space, is now positioned beneath slot 232 and a second single capillary 201 falls into the second space. This process continues until all spaces 221 have been filled.

The transporter 227, with rack 225 now fully loaded with capillaries 201, moves to the extreme right position, in preparation for being unloaded by manipulator 305. During this movement to the rightmost position, rack 225 passes beneath collector 220. If for any reason, one of the spaces 221 was not filled with a capillary during the initial pass beneath collector 220, as rack 225 passes again beneath collector 220 so that the empty spaces will be filled. Furthermore, another detector, for example, a fourth laser sensor 254, is located to the right of collector 220 for detecting and counting the capillaries in rack 225 as rack 225 moves to its rightmost position. If, for instance, after two passes beneath collector 220, the number of capillaries in rack 225 is not correct, fourth laser sensor 254 may send a signal to the PLC unit and the process may be put on hold in anticipation of operator intervention.

Figure 2:
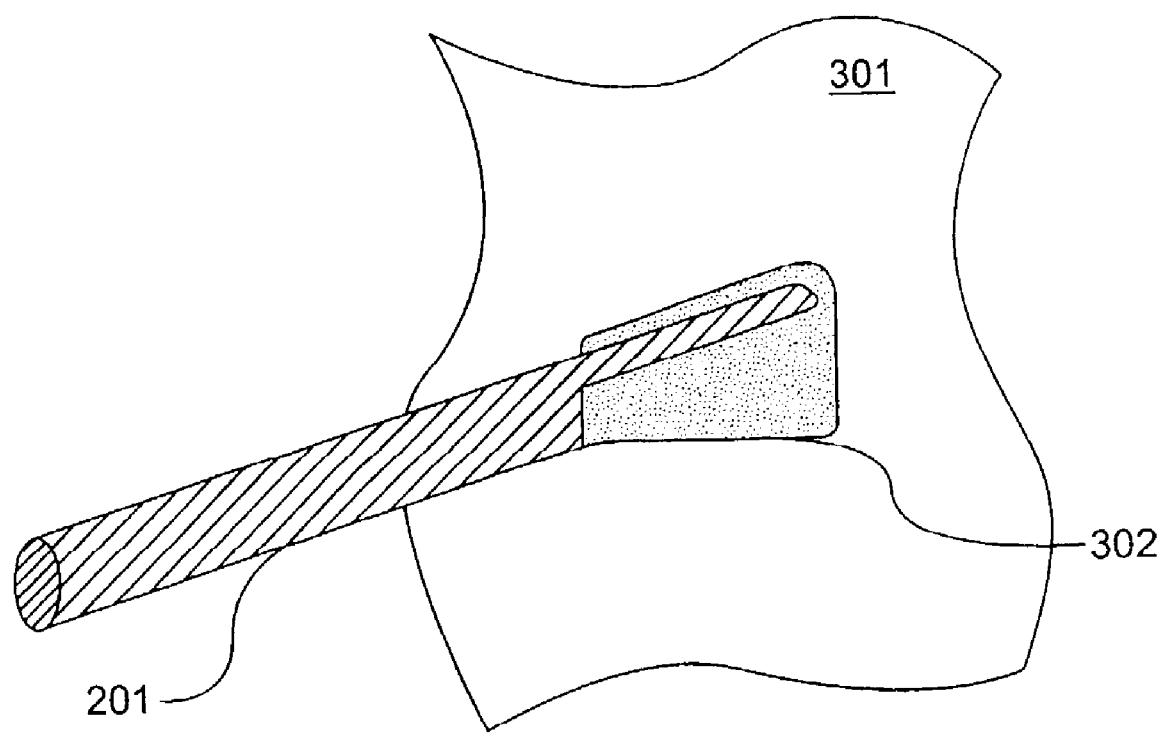
FIG. 2 is a perspective view of a capillary being held by a vacuum finger of the capillary filler system of FIG. 1.
Figure 7:
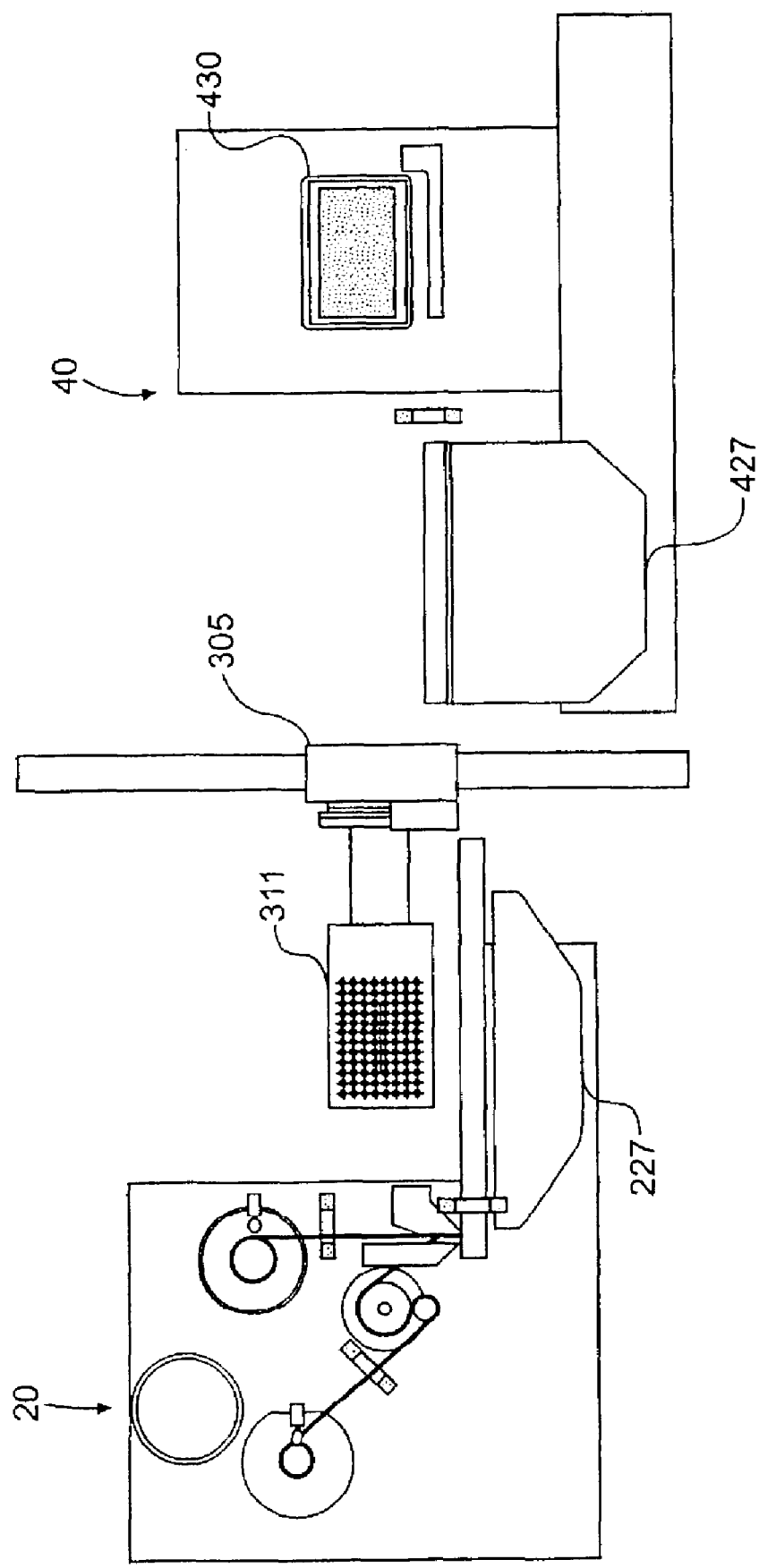
FIG. 7 shows the first transporter of the system of FIG. 5 positioned in front of the gripping unit.

When capillaries 201 are in place on rack 225, the first transporter 227 brings the capillaries from capillary loader subsystem 20 to capillary filler subsystem 30, as shown in FIG. 7. Capillary filler subsystem 30, which functions to automatically fill individual capillaries 201, includes manipulator 305 having gripping unit 311. Gripping unit 311 includes a substantially flat vacuum palm plate 301 accommodating a plurality of vacuum fingers 302 on a front side of plate 301 and a series of separately controllable vacuum manifolds 312 on the back side of plate 301. Vacuum fingers 302 of gripping unit 311 hold capillaries 201 during the filling process. FIG. 2 depicts a typical capillary 201 held by finger 302 on plate 301.

Figure 8:
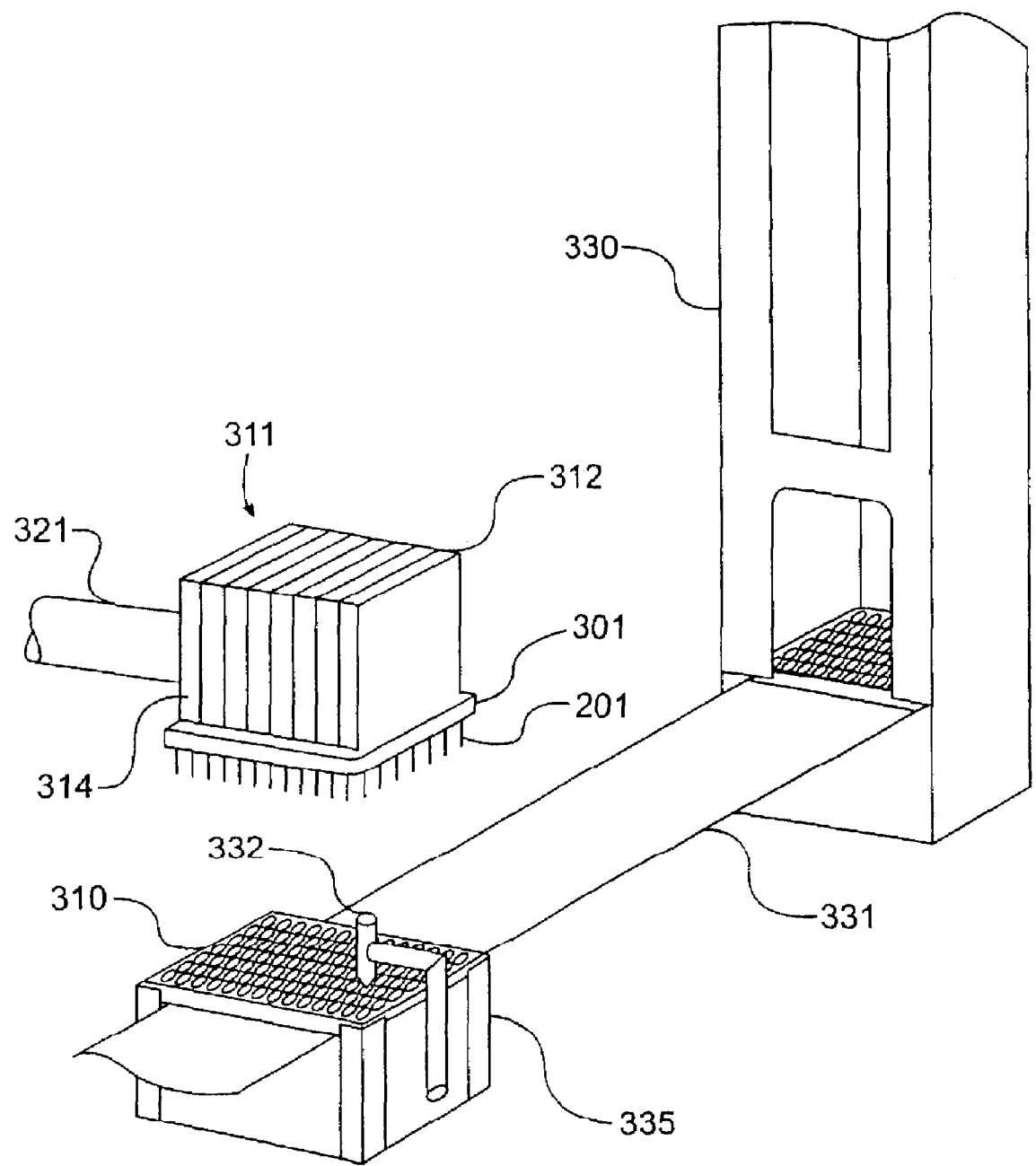
FIG. 8 shows a perspective view of the gripping unit of FIG. 5 at a second station.
Figure 9:
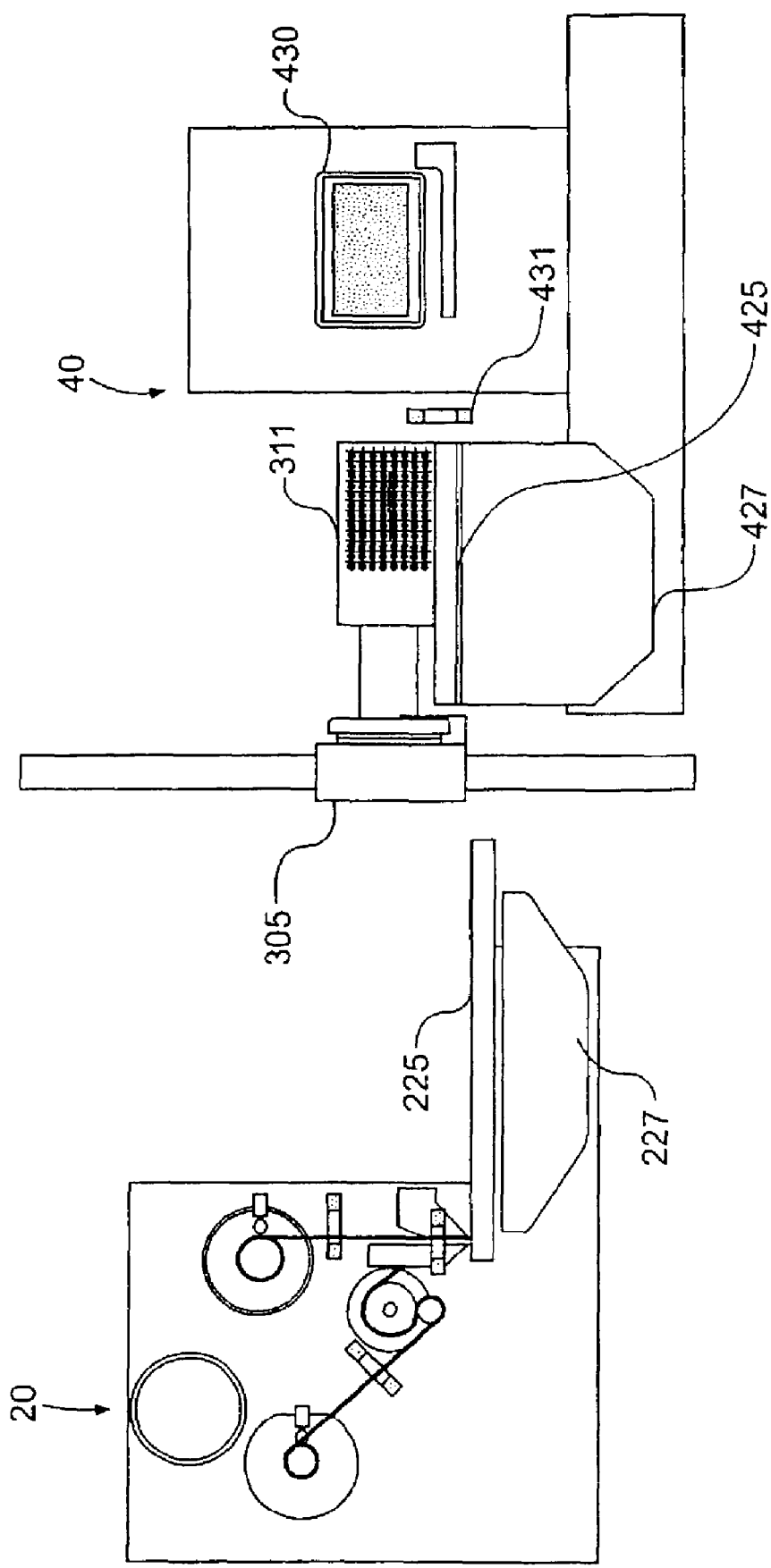
FIG. 9 shows a front view of the capillary filler system of FIG. 5 with the gripping unit at a third station and a second transporter positioned in front of the gripping unit.

FIG. 7 shows gripping unit 311 in a first station for loading capillaries 201 onto plate 301 from first transporter 227. At the first station, gripping unit 311 may move vertically, up and down a central column 320 as depicted by arrow 303. FIG. 8 shows gripping unit 311 in a second station for filling capillaries 201 from library plate 310, such as a standard ninety-six multiwell plate. To move from the first station to the second station, gripping unit 311 rotates around central column 320 as depicted by arrow 306. At the second station, gripping unit 311 may rotate around arm 321 as shown by arrow 307, and move vertically up and down central column 320 as earlier depicted by arrow 303. FIG. 9 shows gripping unit 311 in a third station for unloading capillaries 201 onto second transporter 427. At the third station, gripping unit 311 may move vertically up and down central column 320, also as depicted by arrow 303.

In one embodiment, manipulator 305 is a two axis manipulator, having three degrees of freedom, such as two rotational degrees of freedom and one translational degree of freedom, and a servo-motor associated with each degree of freedom. The Programmable Logic Controller unit may control each of these servo-motors independently. Aternative degrees of freedom associated with manipulator 305 and movements of gripping unit 311, such as may be determined by a person of ordinary skill in the art, may serve to position gripping unit 311 in its desired orientations. For instance, gripping unit 311 could slide horizontally from the first to the second station, rotate around a horizontal hingeline to fill the capillaries and rotate back to its original upright position, and then slide from the second to the third station.

As shown in FIG. 8, gripping unit 311 may include a series of separately controllable vacuum manifolds 312. Each manifold 312 may be vacuum-connected to a plurality of fingers 302. Fingers 302 may be arranged on the front side of plate 301 in a manner that conforms to the axis lines of the wells of a standard library plate. Thus, for instance, gripping unit 311 may include eight vacuum manifolds 312, each vacuum-connected to a row of twelve fingers.

As shown in FIGS. 12(a) and 12(b), fingers 302 may be made out of three plates, for instance, stainless steel, placed side-by-side. The thickness of the middle plate 317 is the same as, or only slightly greater than, the diameter of an individual capillary 201. The thickness of the outside plates 318 may be less, for instance, on the order of half the diameter of capillary 201. The top surface of middle plate 317 is placed below the level of the top surface of outside plates 318, thus creating a groove or depression within which capillary 201 may lie. Moreover, in accordance with one embodiment, a slot 319 extending from the top surface to the back surface is machined into middle plate 317. Slot 319 is airflow-connected to a vacuum channel 313 on the inside of plate 301. The three plates of finger 302 may be welded together at the free end of finger 302.

As shown in FIG. 11, the other end of finger 302 is fixed through a hole in plate 301, the hole being open to a the vacuum channel 313 running within plate 301. The distance between the centerlines of fingers 302 is approximately 9 mm, which corresponds to the pitch center between wells in the standard multiwell plate and which also corresponds to four times 2.25 mm, the centerline-to-centerline distance between capillaries 201 in rack 225.

Thus, fingers 302 in each horizontal row are vacuum-connected to vacuum channel 313 in the inside of plate 301, with each horizontal row of fingers having a separate vacuum channel. These channels 313 are each connected to a venturi valve 314 (one for each row of fingers). Venturi valves 314 may be fixed on the rear of plate 301. A Programmable Logic Controller unit may be used to control each of these valves separately.

When venturi valve 314 is switched on, it creates a vacuum or negative pressure as its output. This vacuum is connected to channel 313, thereby trying to create a vacuum in that channel. However, because fingers 302, themselves, are not airtight, airflow is pulled through these fingers. This airflow will, when capillary 201 is inserted into the groove of finger 302, securely hold the side of capillary 201 against the groove. The airflow is not meant to travel through capillary 201. Slot 319, describe above, may aid in securely holding capillary 201 within the groove of finger 302 by focusing or directing the airflow to the side, rather than to the end, of capillary 201.

Each finger 302 may be approximately one-third of the length of capillary 201. Gripping each capillary 201 along approximately one-third of its length provides adequate gripping force, if the airflow is strong enough, to retain the capillaries when gripping unit 311 is turned horizontally and capillaries 201 hang vertically from fingers 302. As described later, the free, non-gripped ends of capillaries 201 may be inserted into the wells of a library plate to allow for compounds to be picked up via capillary action.

In the first position, gripping unit 311 may move vertically up and down in order to load capillaries 201 from rack 225 to the plurality of horizontal rows of fingers 302 on plate 301. The front side of plate 301 with fingers 302 extending from the front side is placed adjacent a row of capillaries 201 held on rack 225. Starting from the uppermost row of fingers 302, and upon close positioning between an array of capillaries 201 and a row of fingers 302, a slight vacuum pressure is created, by venturi valves or other similar means such as a pump, within finger 302 to lift a row of capillaries 201 off spaces 221 of rack 225 and into fingers 302. As discussed above, typically, about one-third of the length of capillary 201 is held within finger 302, although any suitable portion may be held by finger 302 to securely hold capillary 201.

Gripping unit 311 typically may accommodate eight rows and twelve columns of fingers 302, for a total of ninety-six capillaries. However, any desired number of rows and columns of capillaries may be used with the present invention. A motor (not shown) or other suitable drive mechanism changes the vertical position of the gripping unit 311 on the manipulator 305 as each row of fingers 302 is filled with capillaries 201. Capillaries 201 may fill the rows of fingers of gripping unit 311 from either the top or the bottom so that each row is filled with capillaries. Gripping unit 311 moves vertically to allow the next set of rows access to the next array of capillaries made available by rack 225. The vertical motion of gripping unit 311 loading with capillaries 201 is continued until gripping unit 311 is completely filled with capillaries 201. At this point, stage (a) is completed, as will be explained in more detail below.

In accordance with one embodiment, gripping unit 311, on which twelve by eight fingers are implanted, is positioned in a vertical plane adjacent to rack 225, with the topmost row of fingers 302 just below the level of capillaries 201 on rack 225. The first finger 302 of the topmost row of fingers is positioned directly under the first capillary 201 on the rack. Venture valve 314 associated with this topmost row of twelve fingers is activated. Gripping unit 311 moves vertically until the first row of fingers 302 has passed the level of capillaries 201 on rack 225 by approximately 2 mm. The inflow of air through the fingers of this row allows the fingers to securely take up capillaries from the rack. The first twelve capillaries are now held by the first row of fingers. Since fingers 302 are spaced approximately 9 mm apart and capillaries 201 are space approximately 2.25 mm apart, the fingers of this row have taken up the every fourth capillary of the first forty-eight capillaries on the rack, starting with the first. Gripping unit is then vertically moved up approximately 7 mm (i.e., a total of 9 mm from its original position beneath the level of the capillaries on the rack) to position the second row of twelve fingers just below the level of the capillaries remaining on rack 225. After this approximately 7 mm of vertical movement of gripping unit 311, rack 225 with capillaries 201 is laterally repositioned approximately 2.25 mm further on. The vertical movement of gripping unit 311 may also occur in unison with the lateral repositioning of rack 225 instead of in discrete steps. Thus, the first finger of this second row of fingers is positioned directly below the first capillary of the remaining capillaries (which used to be the second capillary on the rack). Venturi valve 314 associated with this second row of twelve fingers is activated and the subsequent inflow of air through the fingers of this row allows the fingers to take up twelve more capillaries from the rack (again taking every fourth capillary starting with the first remaining capillary on the rack). This sequence is repeated for the third and fourth row of fingers 301 on gripping unit 311. At this time, the first forty-eight capillaries have been loaded onto gripping unit 311.

Rack 225 is laterally moved approximately 98 mm (44 capillary spaces×2.25 mm) plus the length of a gap, if any, between the first and second group of fingers to position the second group of forty-eight capillaries above the fifth row of fingers. The sequence detailed above for the first four rows of fingers is now repeated for the second four rows of fingers. Again in four vertical steps of approximately 9 mm, the last forty-eight capillaries are picked up. At this point, all ninety-six capillaries have been loaded onto gripping unit 311 and all eight venturi valves have been activated.

Figure 4A:
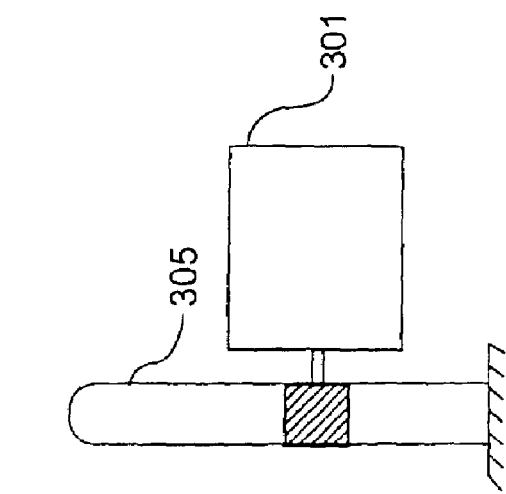
FIG. 4 is a back view of the gripping unit of the capillary filler system of FIG. 1 as it moves through its various stages.
Figure 4B:
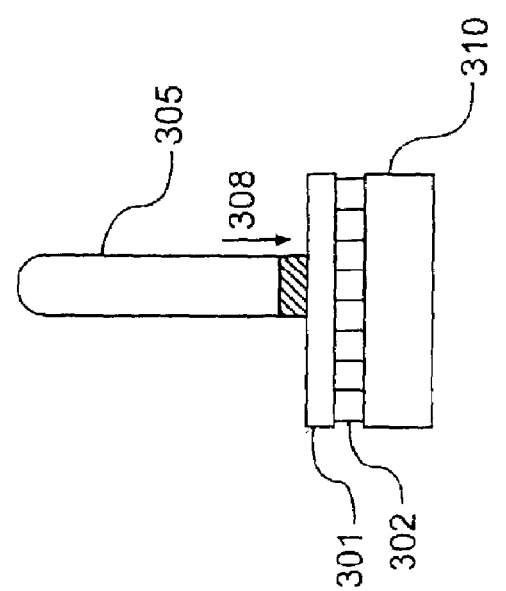
Figure 4C:
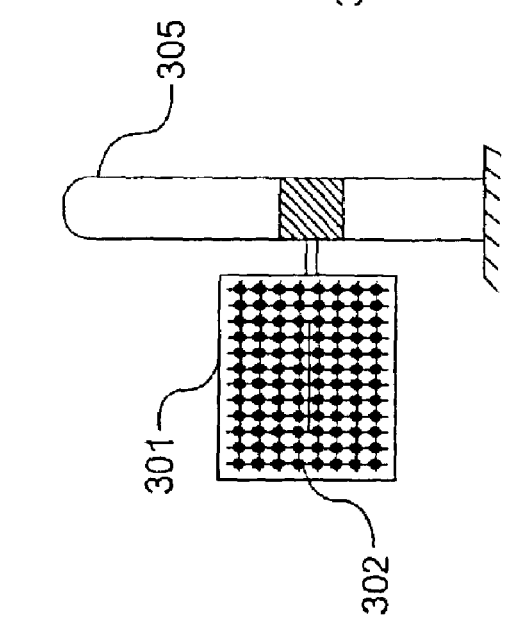
Figure 5:
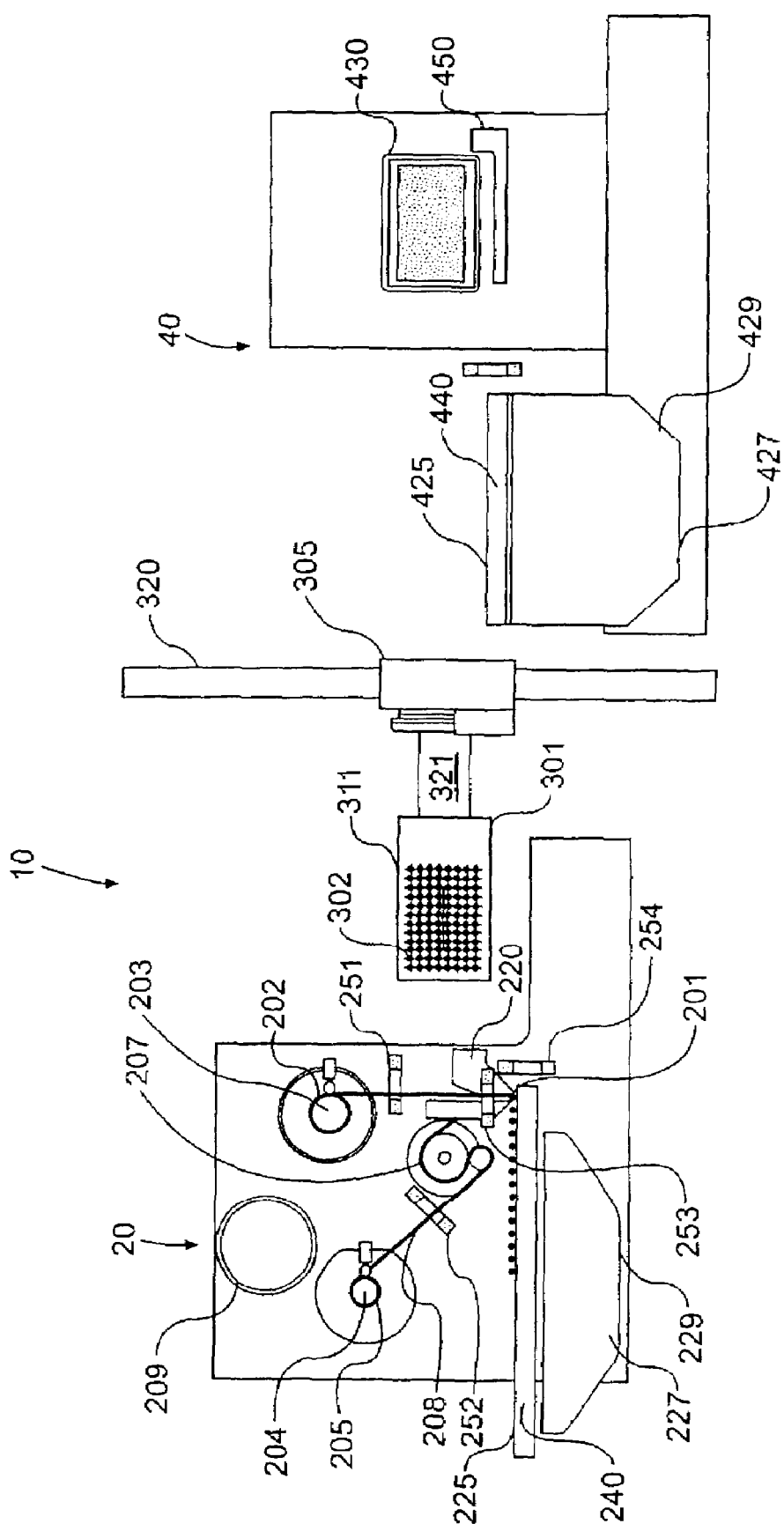
FIG. 5 shows a front view of another exemplary capillary filler system with the gripping unit in at a first station and the first transporter positioned in front of a capillary loading system according to another embodiment of the present invention.

FIGS. 3 and 4 depict a top and a back view, respectively, of system 10 shown in FIG. 1 with respect to the movement of plate 301 through various stages. At stage (a), plate 301 is loaded with capillaries 201. When plate 301 is fully loaded with capillaries 201, manipulator 305 transports plate 301 ninety degrees in the direction of arrow 306, which is with respect to the vertical axis of manipulator 305. The face of plate 301 also is then rotated ninety degrees in the direction of arrow 307 so that capillaries 201 face downward, as depicted in stage (b). At stage (b), with the face of plate 301 with capillaries 201 thereon facing downward, plate 301 is then lowered in the direction of arrow 308 until the tips of capillaries 201 are immersed into compounds contained in, for example, a standard ninety-six well plate 310. Well plate 310 may contain solutions, such as analytes, or other such potential drug candidates or compounds. Furthermore, as described above, the use of the word "standard" with respect to well plate 310, is not meant to limit the well plate to a ninety-six well plate having wells on 9 mm centers. Rather, a "standard multiwell plate" refers to a well plate having a footprint that is commonly used in the screening industry. Currently, this commonly used footprint is 127.8 mm by 85.5 mm. A standard multiwell plate may have a density of ninety-six wells per plate, although other densities, such as sixteen or three-hundred eighty-four, are possible.

In accordance with one embodiment, gripping unit 311 revolves around central column 320 from the first station to the second station, and then rotates around arm 321 so that plate 301 moves from a vertical orientation to a horizontal orientation. In the horizontal orientation, as shown in FIG. 8, fingers 302, with held capillaries 201, point downward. A ninety-six multiwell plate 310 is positioned in a dip-position beneath the capillaries such that the axis lines of the ninety-six capillaries approximately coincide with the center lines of the ninety-six wells of the standard ninety-six multiwell plate 310. Moving gripping unit 311 vertically downward results in the free ends of capillaries 201 entering the solutions in plate 310.

According to one embodiment, a plurality of standard multiwell library plates 310 may be temporarily stored in a stacker 330. At appropriate intervals, the bottom well plate 310 from stacker 330 is moved from the stacker to the second station via a well plate conveyor 331. In other words, conveyor 331 moves a single plate 310 from stacker 330 to the dip-position directly beneath downward facing gripping unit 311. At the second station, a well plate lifter 335 may raise well plate 310 from conveyor 331 so as to position the top surface of the solution in well plate 310 to a known height above conveyor 331. The level of the solution in a reference well may, for instance, be measured by a sensor 332 during the lifting. When the solution in the well is detected by sensor 332, a signal is sent to the PLC unit and well plate lifter 335 is commanded to stop and hold plate 310 at that level. Gripping unit 311 lowers the free ends of capillaries 201 into the solutions; capillaries 201 are filled; and gripping unit 311 raises the capillaries out of the solution. Well plate lifter 335 lowers well plate 310 back onto conveyor 331, which moves the just-used well plate out of the second station and a new well plate into position. Typically, a different well plate may be provided every time gripping unit 311 fills capillaries 201 from the well plate.

Well plates 310 are prepared by placing the same solution or any combination of different solution in the wells of the well plate. A tracking system for remembering and tracking the identity and position of each solution in the capillaries may be implemented. This system first identifies the identity and position of each solution in the wells of the well plate 310. When the capillaries are filled, the tracking system identifies the position in the array of fingers, such as by row and column, and the associated solution in each of the filled capillaries in gripping unit 311. When the filled capillaries are unloaded from gripping unit 311 onto a second transporter 427, the tracking system now identifies and stores the location on the second transporter of each of the filled capillaries and the associated solution. Similarly, when the filled capillaries are assembled onto matrix block 430 their position and identity of the associated solution is remembered and stored. This information is used to identifiy which compound is in which position of the capillaries of the matrix block arrangement when performing assays.

Capillaries 201 are filled with the solutions from well plate 310 by capillary forces. Upon filling of capillaries 201 with a solution, gripping unit 311 is lifted vertically by manipulator 305 back to its original vertical height (as in stages (a) and (c)). The face of plate 301 also is rotated ninety degrees in the direction of arrow 307, and manipulator 305 moves gripping unit 311 ninety degrees in the direction of arrow 306 to stage (c), so that capillaries 201 are visible from the front of the system as depicted in FIG. 1.

The volume of solution filling the capillaries may be predetermined. In general, the volume of solution with any individual capillary will be a function of the viscosity of the solution, the cross-section and volume of the capillary, and the amount of time that the capillary is dipped into the solution. Filling the capillaries does not necessarily mean that the entire capillary volume contains solution, rather the capillaries are "filled," as opposed to being unfilled or empty, when they contain any amount of solution.

In one embodiment, gripping unit 311 vertically moves down to a specific fixed position so that the free end, i.e., the dipping ends, of all capillaries 201 are submerged in the solutions or compounds in well plate 310. The dipping ends of capillaries 201 are submerged in the solutions, typically on the order of approximately 1 mm, until the desired amount of solution has entered the capillaries via capillary forces, typically on the order of a few tenths of a second. The time to fill the capillaries depends, at least in part, upon the viscosity of the solution and the geometry of the capillaries. Gripping unit 311 then moves upward so that all ninety-six filled capillaries are lifted from the standard multiwell library plate.

Gripping unit 311 then rotates around arm 321 a further 90 degrees so that plate 301 is once again in a vertical orientation with capillaries 201 extending horizontally, and then revolves around central column 320 from the second station to the third station. In the third station, gripping unit 311 is ready to discharged or unload capillaries 201 from fingers 302 onto rack 425.

As shown in FIG. 1, matrix packing subsystem 40 receives filled capillaries 201 at stage (c) and includes a second transporter 427 having a toothed conveyor or rack 425. Rack 425 receives the filled capillaries 201 in spaces 421 in substantially the opposite manner as the loading of the capillaries 201 onto gripping unit 311 at stage (a). The filled capillaries are deposited, row by row, from fingers 302 onto spaces 421, and the resulting array of capillaries 201 are then moved by transporter 427 to close proximity to a capillary matrix block 430.

Second transporter 427 may include a horizontal servo driven slide, such as first transporter 227 had, and a rack 425. A servo-motor, controlled by the Programmable Logic Controller unit, may drive the spindle. Similarly to transporter 227, the accuracy with which rack 425 is to be positioned relative to gripping unit 311, during the filled capillary unloading process, will typically be on the order of approximately 0.1 mm.

Figure 10:
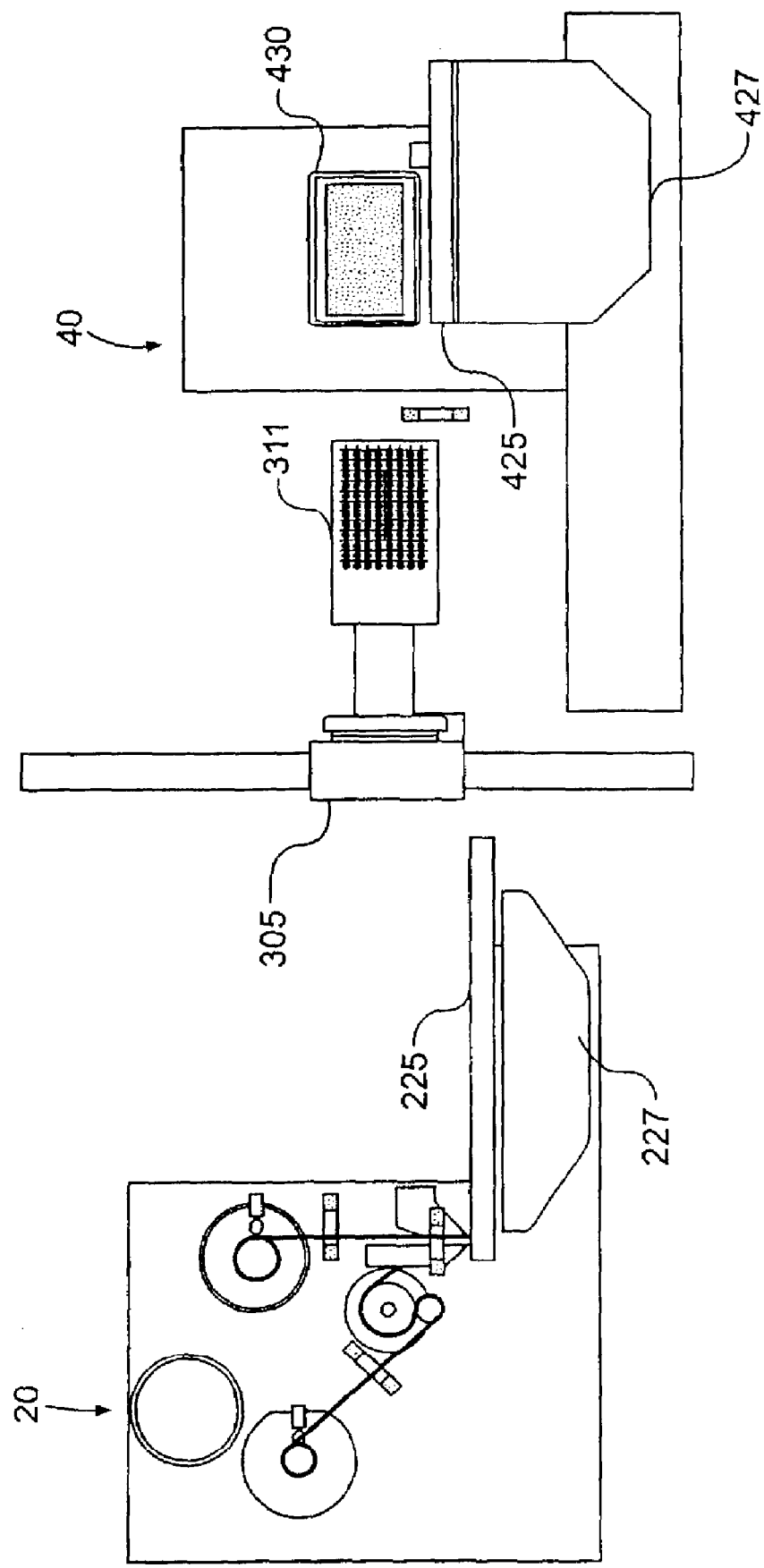
FIG. 10 shows the second transporter of FIG. 9 positioned in front of the matrix block.
Figure 16A:
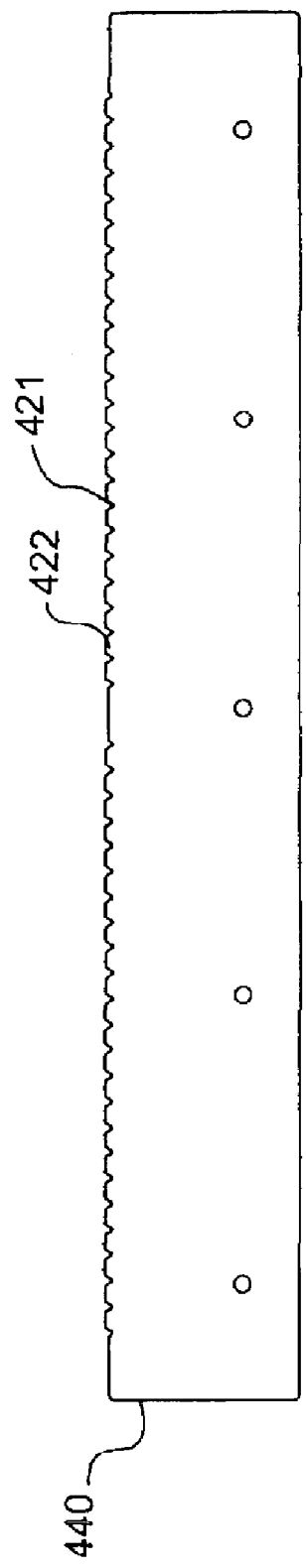
FIGS. 16(a) and 16(b) show alternative embodiments of a rack for the second transporter of FIG. 5.
Figure 16B:
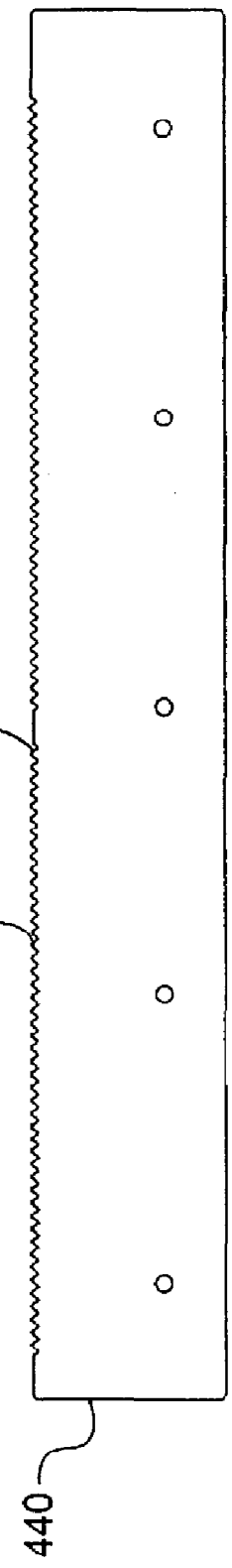

As shown in FIGS. 9 and 10, rack 425 may be made out of two plates 440 that are fixed on both sides of a transport table 429. Transport table 429 and racks 425 may be configured to let a lifter 450 pass between plates 440 and under the row of capillaries held in rack 425. Plates 440 may be made from stainless steel, brass, plastic, or any other material capable of having spaces 421 machined between teeth 422. Plates 440 may have a thickness of, for instance, approximately 0.1 mm, and their length may be such as to accommodate ninety-six spaces 421 and teeth 422, in two groups of forty-eight (as shown in FIG. 16(b)) with a gap on the order of a one or two centimeters in between the two groups of capillaries along the length of the plates. The centerline-to-centerline distance between spaces 421 may be consistent with the distance between filled capillaries in the matrix block 430 for example, approximately 2.25 mm for a 1536 capillary template. Alternatively, the length of plates 440 may be such as to accommodate forty-eight spaces in two groups of twenty-four (as shown in FIG. 16(*b*)). This grouping would be consistent with, for instance, a matrix block for a 384 capillary template. Teeth 422 may be deeper or more explicit than teeth 222 on rack 225, allowing capillaries 201 to lie below the top surface of rack 425. This may be advantageous, especially where only the weight of capillaries 201 retain the capillaries in the spaces between the teeth of the rack.

Unloading the ninety-six filled capillaries esssentially takes place in the reverse order as the loading of the ninety-six empty capillaries in the loading part. Therefore, by starting from the bottom row of fingers 302 on gripping unit 311 and sequentially moving gripping unit vertically downward and transporter 227 laterally, and at the same time by sequentially de-activating the eight venturi valves, the ninety-six filled capillaries 201 may be accurately released from gripping unit 311 and deposited in spaces 421 of rack 425.

When gripping unit 311 and transporter table 429 are in the unload position, unloading can start. Spaces 421 of rack 425 are aligned with the bottom row of filled capillaries 201 held by gripping unit 311. Gripping unit 311 moves vertically downward until capillaries 201 in this bottom row are positioned within spaces 421 between the teeth of rack 425. The venturi valve, or other vacuum unit, associated with the bottom row of fingers is switched off and airflow through the fingers stop, thereby releasing the filled capillaries. Gripping unit 311 continues to move vertically downward until the top of the bottom row of fingers is beneath the row of capillaries just laid in the rack. Transporter table moves laterally one space over so that, again, empty spaces 421 of rack 425 are aligned with the next row of filled capillaries held by gripping unit 311. Repeating the above discussed unloading sequence for the bottom row of fingers, gripping unit 311 moves vertically downward until the filled capillaries in this second from the bottom row are positioned within spaces 421. The venturi valve associated with the second from the bottom row of fingers is switched off and airflow through the fingers stop, thereby releasing the filled capillaries. Gripping unit 311 continues to move vertically downward until the top of the second from the bottom row of fingers is beneath the row of capillaries in the rack. Transporter table moves laterally one space over so that, again, empty spaces 421 of rack 425 are aligned with the next row of filled capillaries held by gripping unit 311. And so on, until all filled capillaries 201 have been unloaded from gripping unit 311 onto rack 425.

Second transporter 427 fully loaded with filled capillaries 201 then moves laterally to position the filled capillaries 201 on rack 425 in front of capillary matrix block 430. As transporter 427 moves to position the filled capillaries in front of matrix block 430, a detector, such as a fourth laser sensor 431, may check if every space 421 of rack 425 has a filled capillary. If this fourth sensor 431 detects a missing capillary or an unfilled capillary in rack 425, it sends a signal to the controller circuit, such as the Programmable Logic Controller unit. In response to this error signal, for instance, movement of transporter 427 could be stopped and an operator could manually fix the error.

Capillary matrix block 430 serves as a housing for filled capillaries 201. One embodiment for matrix block 430 is described in U.S. patent application Ser. No. 09/426,708 entitled "Device and Related Method for Dispensing Small Volumes of Liquid" and filed Oct. 26, 1999, the entire disclosure of which is expressly incorporated herein by reference. Matrix block 430 has, for example, forty-eight columns and thirty-two rows to accommodate 1,536 filled capillaries 201. Importantly, any desired number of columns and rows of filled capillaries may be used to form matrix block 430. Filled capillaries 201 may be affixed to matrix block 430 using a suitable adhesive or any other fixing mechanism.

Figure 13:
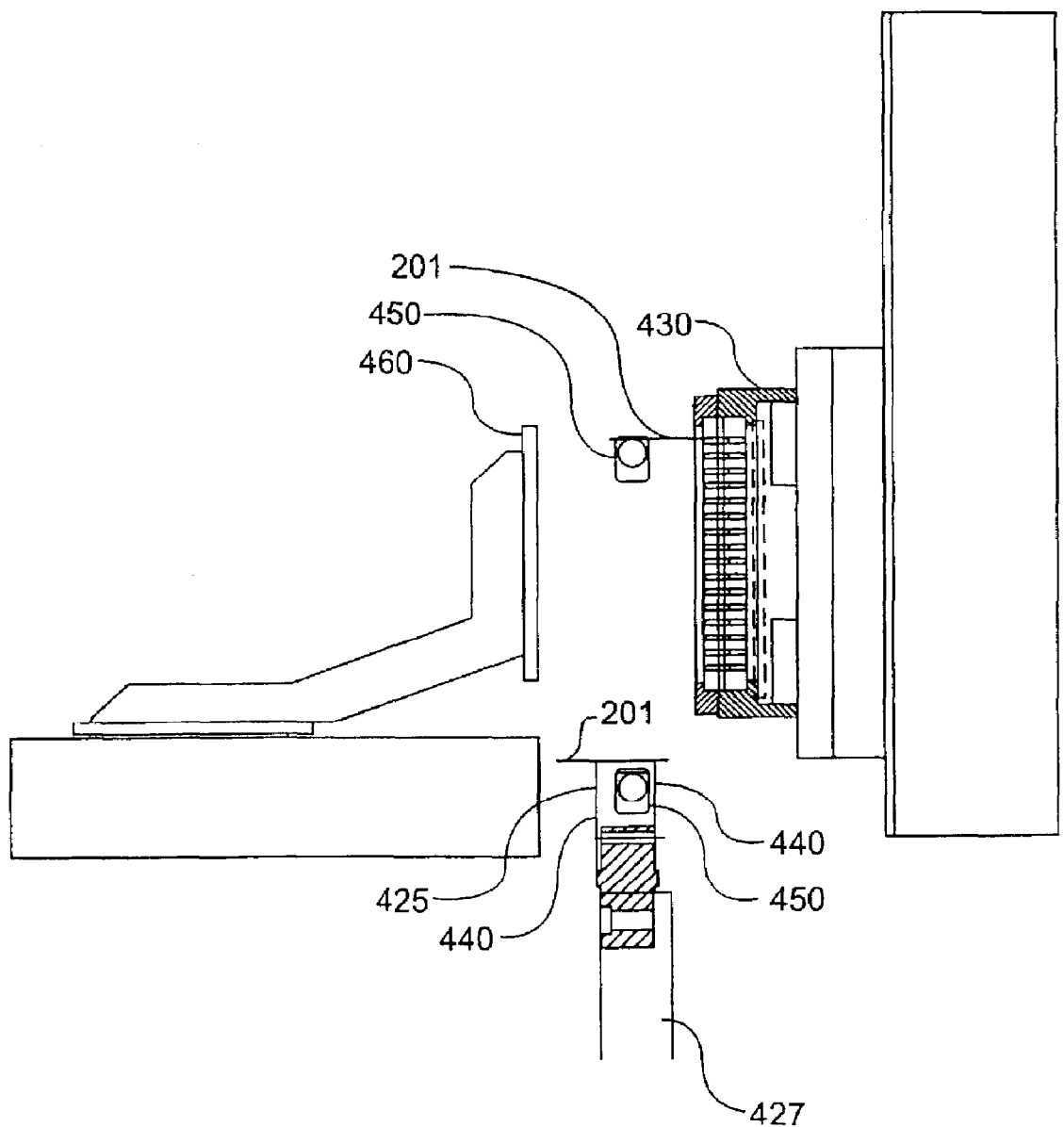
FIG. 13 shows a side view of the matrix packer subsystem of FIG. 5 with the lifter in both a lowered position and a raised position.

As shown in FIGS. 10 and 13, the horizontal servo driven slide for tranporter 427 may position rack 425 with ninety-six filled capillaries opposite matrix block 430. The matrix array (comprising, for instance, forty-eight columns and thirty-two rows for the 1536 template) is in a fixed vertical position. The ninety-six filled capillaries on rack 425 form two groups of forty-eight capillaries, each group to be inserted as a row into matrix block 430. Thus, the ninety-six filled capillaries will be inserted in two stages using a lifter 450 and a pushing plate 460.

Lifter 450 is positioned in front of matrix block 430 and is configured to pass between plates 440 and under the row of capillaries held in rack 425. Pushing plate 460 is also positioned in front of matrix block 430. Lifter 450 takes forty-eight capillaries from rack 425 and vertically lifts them to the level where they will be placed in the capillary matrix block 430. Pushing plate 460, moving horizontally and in a series of two pushes, pushes the forty-eight lifted capillaries, all at one time, into a row in matrix block 430. The first horizontal push by pushing plate 460 causes the row of forty-eight filled capilllaries to be partially inserted into matrix block 430, but stops before pushing plate 460 contacts lifter 450. Lifter 450 may then be vertically lowered and the forty-eight partially inserted capillaries will not fall out of matrix block 430. Lifter 450 is lowered until it no longer impedes the horizontal movement of pushing plate 460, and plate 460 performs a second horizontal push of the partially inserted capillaries, thereby causing the capillaries to be fully inserted into matrix block 430.

FIG. 14 illustrates an exemplary lifter 450 with notches 451. In accordance with one embodiment, lifter 450 may be configured as a rack structure with the same number of notches 451 as there are columns in the array of matrix block 430, for instance, forty-eight notches for a forty-eight by thirty-two array, i.e., a 1536 array. Notches 451 may be V-shaped notches. The center-to-center distance between notches 451 may be approximately 2.25 mm for a 1536 array. In another embodiment, each notch 451 has a hole 452 at the base of the notch. Holes 452 may be flow-connected to a vacuum maniflold chamber 453, which may be a channel machined within the body of lifter 450. Chamber 453 may be connected to a vacuum generator (not shown), which may be controlled by the Programmable Logic Controller unit.

In operation, lifter 450 may be attached to a high accuracy linear motor, also controlled by the Programmable Logic Controller unit, that moves lifter 450 up and down. Originally positioned at the bottom of its vertical travel, the lateral movement of transporter 427 places lifter 450 between plates 440 and below the horizontal level of the row of filled capillaries in rack 425. The width of lifter 450 is less than the distance between plates 440. Notches 451 are vertically aligned with the first forty-eight capillaries resting in rack 425. Lifter 450 moves vertically upward such that the first forty-eight capillaries of rack 425 are contacted by notches 451, and further upward movement of lifter 450 causes the capillaries to be lifted off of rack 425. A vacuum pressure within chamber 453, which is flow-connected to holes 452 at the base of notches 451, may assist in the retention of the capillaries by lifter 450. Moreover, this vacuum pressure may assist in the precision alignment of the capillaries by pulling the capillaries against the sides of the V-shaped notches in such a way that all the central lines of the capillaries are in one plane, with a center-to-center distance of approximately 2.25 mm. Lifter 450 positions the forty-eight capillaries vertically in accordance with the thirty-two positions of the grid structure template, such that the central lines of the capillaries coincide with the forty-eight holes of the first topmost row of matrix block 430. This vertical alignment between notches 451 and the holes for the filled capillaries in capillary matrix block 430 may be facilitated by mechanically aligning lifter 450 prior to the lifting operation.

Once the row of forty-eight capillaries on lifter 450 are aligned with the holes in matrix block 430, the capillaries are pushed in the direction of matrix block 430 by pushing plate 460. Pushing plate 460 may be coupled to a linear, servo unit controlled by the Programmable Logic Controller unit. Although, a vacuum pressure is provided within chamber 453 and to notches 451, the capillaries are axially slidable within the notches. The forty-eight capillaries are substantially simultaneously partially inserted axially into matrix block 430 perforations. The vacuum generator providing vacuum pressure to chamber 453 is switched off, thereby releasing the capillaries from lifter 450. Lifter 450 is moved vertically downward to its originally position between plates 440, so as to clear the area between pushing plate 460 and matrix block 430. Pushing plate 460 then re-engages the row of forty-eight partially inserted capillaries and substantially simultaneously pushes the row of capillaries until they are fully inserted.

Transporter 427 then moves laterally to position the next forty-eight filled capillaries on rack 425 into vertical alignment with notches 451 of lifter 450. The movements of lifter 450 and pushing plate 460 described above are repeated and the second row of filled capillaries is inserted in matrix block 430. Transporter 427 moves laterally back to the third station, to a position in front of gripping unit 311, which has become fully loaded with filled capillaries. Gripping unit 311 unloads the filled capillaries onto rack 425 as previously described, transporter 427 moves laterally to reposition itself in front of matrix block 430, and the process repeats itself until all thirty-two rows of forty-eight capillaries have been inserted into capillary matrix block 430. The insertion of filled capillaries into matrix block 430 takes place from the top row to the bottom row.

In one embodiment, capillary matrix block 430 includes three parts: a primary capillary holder 432, a secondary capillary holder 433, and a frame 434. According to an embodiment, capillary matrix block 430 mechanically retains the filled capillaries in the array without the use of an adhesive fixer or other fixing mechanism. The format of the array defined by matrix block 430 may be the same format as a standard well plate, a high-density well plate, or other non-standard formats. Starting from a collection of unfilled capillaries, the present invention is able assembly these unfilled capillaries into an array for filling the capillaries from a well plate, and then to reassemble the now-filled capillaries into a capillary matrix block having any standard or non-standard arrangement of the capillaries. When matrix block 430 and the corresponding test plate are put together, the free end of every filled capillary 201 may extend into the middle of a well in the test plate.

Frame 434 holds the primary and secondary capillary holders 432, 433. Frame 434 may provide a consistent mounting for insertion into matrix packing subsystem 40. The consistent mounting of frame 434 may facilitate the setup and removal of capillary matrix block 430 in subsystem 40. For instance, frame 434 and subsystem 40 may be configured such that there is only one way to insert frame 434 into subsystem 40, thereby guaranteeing a more consistent fit and reducing the need to have to manually adjust the alignment settings of lifter 450 after every assembly.

As shown in FIG. 15, primary capillary holder 432 may be configured as a matrix template comprising a thin sheet, which defines the array of capillary holes 435 of matrix block 430. Primary capillary holder 432 may be made of a stainless steel sheet, for instance, approximately 0.1 mm thick. The centers of each capillary hole 435 may be designed to substantially match the centers of the wells in the test plates that will be used with capillary matrix blocks 430. Holes 435 may be machined in the sheet.

In accordance with one embodiment, as shown in FIG. 15, holes 435 with spring elements 436 may be photo-etched into holder 432. Photo-etching may be used to remove material from holder 432 to form, for instance, three loops 437, or any other shape to provide retaining force, within holes 435. Moreover, each loop 437 may be partially etched so that the loop itself is less than the thickness of the sheet material forming holder 432. Spring elements 436 may be configured to mechanically retain the filled capillaries to the template. Spring elements 436 deflect, either elastically and/or plastically, to allow the capillary to slide through hole 435, yet provide sufficient force to hold capillaries 201 in holes 435 when matrix block 430 is in use. Spring elements 436 may allow individual capillaries 201 to slide axially relatively easily so that the array of capillaries may match the profile of the bottom of the wells in the test plate. Other mechanical or non-mechanical methods, such as adhesive, may be used to retain the filled capillaries to the template.

Secondary capillary holder 433 may be formed from two sheets of metal or plastic or any other suitable material, which lie on either side of primary capillary holder 432.

The sheets may be, for instance, on the order of approximately 7 mm thick. Each of these sheets has an array of holes that is substantially identical to the hole pattern in primary capillary holder 432. The holes in secondary holder 433 may be approximately 0.1 mm wider than the diameter of capillary 201. On one side of each sheet the holes may have a chamfered edge, which may be, for instance, approximately three times the diameter of capillary 201. The chamfer in the top plate may face away from primary capillary holder 432 and may be to guide capillary 201 through the layers of the primary and secondary capillary holders. The chamfer in the bottom plate may face toward primary capillary holder 432 and may serve as a relief area for deflection of spring elements 435.

It will be apparent to those skilled in the art that various modifications and variations can be made to the disclosed embodiments without departing from the spirit or scope of the invention. For example, the unfilled capillaries need not be provided on a tape roll. Or, a single transporter could be used instead of the two transporters described above. Alternatively, the manipulator could have fewer or more degrees of freedom and different movable axes as could be designed by a person of ordinary skill in the art. Moreover, the matrix block need not arrange the filled capillaries in a rectangular matrix. For instance, if appropriate modifications are made to the racks and to the lifter and/or to the movements of the matrix block relative to the lifter, the matrix block could have capillaries arranged in a circular or radial pattern. Further, for instance, the holes, and if desired, the spring elements in the capillary holder could be formed by other precision machining techniques.

Thus, it is intended that the present invention cover such modifications and variations of the disclosed embodiments that are within the scope of the appended claims and their legal equivalents.

We claim:

1. A system for creating a matrix of solution-filled capillaries comprising:
 a capillary loader means for loading a plurality of unfilled capillaries onto a first transporter, wherein the unfilled capillaries are provided in a rolling tape;
 a manipulator means for collecting the plurality of unfilled capillaries from the first transporter, filling the plurality of capillaries with at least one solution, and unloading the plurality of filled capillaries onto a second transporter; and
 a matrix packer means for collecting the plurality of filled capillaries from the second transporter and inserting the plurality of filled capillaries into a matrix template;
 characterized in that the capillary loader includes
 an unwinder to unwind the rolling tape (202) carrying the unfilled capillaries, said unwinder comprising a loading peg (203);
 a mechanism to release the capillaries from the rolling tape
 a winder for rewinding the rolling tape (204) after the capillaries are released, said winder comprising a rewinding peg (205); and
 a motor (209) which turns pegs (203) and (205) via a rotary dashpot or a slip coupling, or other similar suitable mechanisms.

2. The system of claim 1 wherein the first transporter includes a plurality of equidistant spaces, each space holding one tube, and the second transporter includes a plurality of equidistant spaces, each space holding one tube.

3. The system of claim 2, wherein the centerline-to-centerline distance between the plurality of equidistant spaces on the first transporter is approximately 2.25 mm.

4. The system of claim 1, wherein the manipulator includes a gripping unit means for moving to a first station to collect the plurality of capillaries, moving to a second station to fill the plurality of capillaries, and moving to a third station to unload the plurality of filled capillaries.

5. The system of claim 4, wherein the gripping unit collects the plurality of capillaries from the first transporter with an array of fingers, and wherein the centerline-to-centerline distances between the fingers substantially correspond to the centerline-to-centerline distances between wells of a library well plate containing the at least one solution.

6. The system of claim 5, wherein the fingers use vacuum-generated air flow to retain the capillaries.

7. The stem of claim 1, wherein the manipulator includes a gripping unit having an array of fingers for collecting the plurality of capillaries, the fingers being arranged in rows and the centerline-to-centerline distance between adjacent fingers in a row being an integer multiple of the centerline-to-centerline distance between adjacent capillaries on the first transporter.

8. The system of claim 7, wherein the centerline-to-centerline distance between adjacent fingers is approximately 9 mm.

9. The system of claim 1, wherein the loader loads ninety-six unfilled capillaries onto the first transporter, the manipulator fills all ninety-six capillaries at substantially the same time, and the matrix template receives ninety-six or an integer multiple thereof of filled capillaries.

10. The system of claim 9, wherein the matrix template receives an array of forty-eight columns by thirty-two rows of filled capillaries.

11. The system of claim 1, wherein the matrix template includes spring elements for retaining the filled capillaries to the matrix template.

12. The system of claim 1, wherein the matrix packer includes a lifter means for collecting the plurality of filled capillaries from the second transporter and position the plurality of filled capillaries in front of a corresponding plurality of holes in the matrix template.

13. The system of claim 1, wherein the plurality of capillaries are filled with at least one solution that is stored in a standard multiwell plate having a first density of wells per plate, and wherein the matrix template is configured to hold the plurality of filled capillaries in an array that corresponds to a standard multiwell plate having a second density of wells per plate.

14. The system of claim 1, wherein the plurality of capillaries are filled with at least one solution that is stored in a standard multiwell plate, and wherein the matrix template holds the plurality of filled capillaries in an array that corresponds to a non-standard multiwell plate.

* * * * *